US012760307B2

(12) United States Patent
Yoon

(10) Patent No.: US 12,760,307 B2
(45) Date of Patent: Oct. 13, 2026

(54) MORPHOLINO OLIGONUCLEOTIDE DERIVATIVES

(71) Applicant: Nexoligo Co., Ltd., Anyang-si (KR)

(72) Inventor: Yeohong Yoon, Seoul (KR)

(73) Assignee: NEXOLIGO CO., LTD., Anyang-si (KR)

( * ) Notice: Subject to any disclaimer, the term of this patent is extended or adjusted under 35 U.S.C. 154(b) by 643 days.

(21) Appl. No.: 18/007,830

(22) PCT Filed: Jun. 7, 2021

(86) PCT No.: PCT/KR2021/007101
§ 371 (c)(1),
(2) Date: Dec. 2, 2022

(87) PCT Pub. No.: WO2021/246846
PCT Pub. Date: Dec. 9, 2021

(65) Prior Publication Data

US 2023/0235328 A1 Jul. 27, 2023

(30) Foreign Application Priority Data

Jun. 5, 2020 (KR) ........................ 10-2020-0068631

(51) Int. Cl.
*C12N 15/113* (2010.01)
*C07F 9/6561* (2006.01)

(52) U.S. Cl.
CPC .......... *C12N 15/113* (2013.01); *C07F 9/6561* (2013.01); *C12N 2310/3233* (2013.01)

(58) Field of Classification Search
None
See application file for complete search history.

(56) References Cited

U.S. PATENT DOCUMENTS 5,185,444 A 2/1993 Summerton et al.

FOREIGN PATENT DOCUMENTS

| | | |
|---|---|---|
| KR | 10-1598423 | 3/2016 |
| KR | 10-2016-0082972 | 7/2016 |
| KR | 10-2018-0084748 | 7/2018 |
| KR | 10-2019-0027907 | 3/2019 |
| WO | 2019-060862 | 3/2019 |

OTHER PUBLICATIONS

KIPO, PCT Search Report & Written Opinion of Application No. PCT/KR2021/007101, Sep. 2, 2021.

Bhadra. J. et al., "Synthesis of Morpholino Monomers, Chlorophosphoramidate Monomers, and Solid-Phase Synthesis of Short Morpholino Oligomers", Current Protocols in Nucleic Acid Chemistry. 2015. Supplement 62. Unit 4.65. pp. 4.65.1-4.65.26., Sep. 2015.

Taylor. M. F. et al., "In Vitro Efficacy of Morpholino-modified Antisense Oligomers Directed against Tumor Necrosis Factor-α mRNA", Journal of Biological Chemistry. 1996. vol. 271. No. 29., pp. 17445-17452, Jul. 1996.

Kang. H. et al., "Stacking interactions of ApA analogues with modified backbones", Biopolymers: Original Research on Biomolecules. 1992. vol. 32. pp. 1351-1363., Oct. 1992.

Bappaditya Nandi et al., "Synthesis of Nucleobase-Functionalized Morpholino-Modified Nucleoside Monomers Through Palladium-Catalyzed Cross-Coupling Reactions", European Journal of Organic Chemistry 2013.7 (2013): 1271-1286, Jan. 2013.

Varizhuk, Anna M., et al., "Synthesis of oligonucleotides containing novel G-clamp analogue with C8-tethered group in phenoxazine ring: Implication to qPCR detection of the low-copy Kemerovo virus dsRNA." Bioorganic & medicinal chemistry 25.14 (2017): 3597-3605, Jul. 2017.

Hu, Jiaxin, et al., "Cellular localization and allele-selective inhibition of mutant huntingtin protein by peptide nucleic acid oligomers containing the fluorescent nucleobase [bis-o-(aminoethoxy) phenyl] pyrrolocytosine." Bioorganic & medicinal chemistry letters 19.21 (2009): 6181-6184, Nov. 2009.

R. H. E. Hudson et al., "A direct synthesis of pyrrolocytosine from 5-iodocytosine." Nucleosides, Nucleotides and Nucleic Acids 24.5-7 (2005): 581-584, 2005.

Smith, Temple F. et al., "Comparison of biosequences." Advances in applied mathematics 2.4 (1981): 482-489, Dec. 1981.

Sankha Pattanayak et al., "Improved Protocol for the Synthesis of Flexibly Protected Morpholino Monomers From Unprotected Ribonucleosides", Nucleosides, Nucleotides and Nucleic Acids 31, (2012): 763-782, Nov. 2012.

Leena M. Patil et al., "Effective and Regioselective 5-Iodination of Pyrimidine Bases and Corresponding Nucleosides by an Inexpensive Iodine-Sodium Nitrite Reagent" heterocyclic letter vol. 4: (4), 2014, 559-564, 2014.

Rom, J., et al., "Oblimersen combined with docetaxel, adriamycin and cyclophosphamide as neo-adjuvant systemic treatment in primary breast cancer: final results of a multicentric phase I study." Annals of oncology 19.10 (2008): 1698-1705, May 2008.

*Primary Examiner* — Noble E Jarrell
(74) *Attorney, Agent, or Firm* — LEX IP MEISTER, PLLC

(57) ABSTRACT

The present invention relates to a novel morpholino oligonucleotide comprising at least one type of morpholino nucleotide monomer having pyrrolocytosine (pC) among unnatural cytosines, and relates to a morpholino oligonucleotide capable of more selectively binding to a target RNA and exhibiting excellent cell penetration compared to an MPO having a natural cytosine, and thus being capable of greatly contributing to the development of a therapeutic agent for incurable diseases in the area of morpholino oligonucleotides.

2 Claims, 1 Drawing Sheet

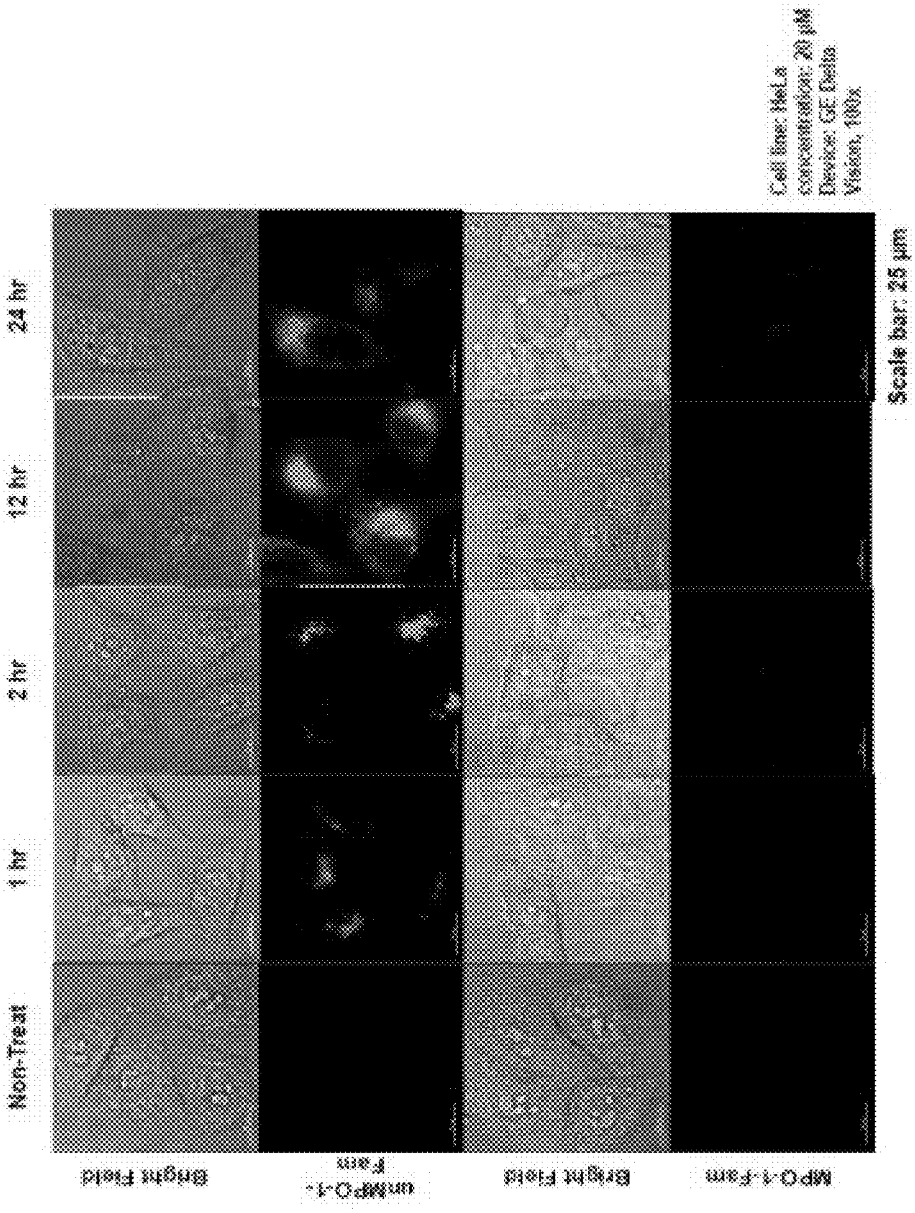
Non-Treat
1 hr
2 hr
12 hr
24 hr
Bright Field
unMPO-1-Fam
Bright Field
MPO-1-Fam
Cell line: HeLa
concentration: 20 μM
Device: GE Delta Vision, 100x
Scale bar: 25 μm

MORPHOLINO OLIGONUCLEOTIDE DERIVATIVES

TECHNICAL FIELD

The present invention relates to a novel morpholino oligonucleotide derivative that has been chemically modified so as to exhibit superior cell penetration and strong nucleic acid affinity. More specifically, the present invention relates to a novel morpholino oligonucleotide derivative containing at least one type of nucleotide monomer having pyrrolocytosine (pC) in the field of unnatural nucleic acid base, especially among unnatural cytosine, wherein the morpholino oligonucleotide consists of a phosphorodiamidate bond between morpholino nucleotide monomers and exhibiting very good cell penetration property, and thus being capable of being used for various biological purposes including gene therapeutic agent.

BACKGROUND ART

Antisense oligonucleotide (referred to as ASO) is a single-chain type polymer substance in which a number of nucleotide units mainly made through organic synthesis are polymerized, which is an artificial gene capable of forming Watson-Click base pair with the target RNA in the cell. Due to such characteristics, it has been widely known that ASO can inhibit the production of unwanted proteins while binding to a specific portion of the target RNA, and thus can be applied to the treatment of diseases at a genetic level. Recently, it has been reported that ASO can make a mRNA slightly modified through an alternative splicing process with a precursor RNA present in the nucleus, i.e., by being unable to bind to a specific genetically deficient exon, followed by exon skipping and exon ligation. Taking advantage of the exon skipping characteristics in this way, the development of therapeutic agents for genetic diseases in a new field, which can restore a specific protein whose function has been lost due to a genetic disease having a specific exon-defective gene to a protein slightly modified so that it can newly function, is actively promoted.

Meanwhile, modified oligonucleotides having very diverse structures have been known until now. Starting from methylphosphonate oligonucleotide which is the initial derivative, phosphorothiolate oligonucleotide, phosphoramidate oligonucleotide, and the like are derivatives obtained by modifying a linker between monomers.

In addition, dozens of derivatives, such as 2'-OMe, 2'-O-MOE, 2'-F-RNA, and LNA, have been known as examples of modified sugar structures.

And, typical examples of a specific structure that does not have a sugar structure are PNA (peptide nucleic acid) and MPO (morpholino oligonucleotide).

In addition, many studies have been conducted on siRNA-based RNAi therapeutic agents.

As described above, gene therapeutic agents using various oligonucleotides in terms of the structure and the preparation method are being developed in many areas, but in order for the artificial genes to be used as therapeutic agents, the following necessary and sufficient conditions are required.

1) It must be stable to the nuclease enzyme within a cell; 2) it must maintain relatively long-lasting efficacy, that is, complementary binding to the target gene and inhibit protein expression; 3) it must have excellent solubility in water; 4) it must have low toxicity, and in particular, toxicity caused by binding to in vivo protein must be eliminated; and 5) no mismatch must exist by having high selectivity with the target gene.

Among the derivatives that satisfy all the conditions essential for gene therapeutic agents in this way, the aforementioned MPO is a representative example. MPO is a neutral substance in which the linker, which is the backbone, does not have ionic characteristics, and is a derivative of a gene therapeutic agent with excellent solubility.

Particularly, the MPO is included in the region of ASO, which has very good solubility compared to PNA, and which has characteristics capable of being prepared without self-aggregation even to 25mers or more.

Similar to PNA, MPO is an artificial gene derivative that complementarily binds to a target gene and inhibits protein production by steric blocking during the translation process. The general structure of the MPO is as follows.

[General Structure of MPO]

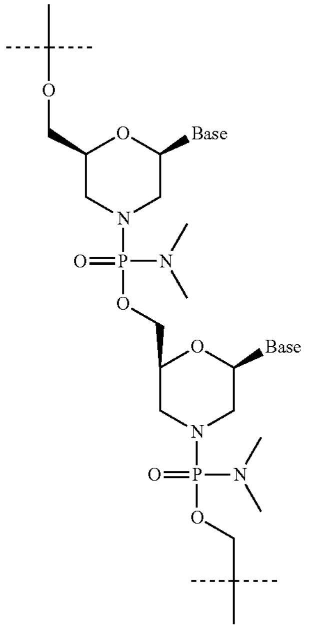

Until now, indications that can be treated using MPO have been widely known. This is due to the mechanism of action that inhibits the translation of a specific protein by a complementary binding to target mRNA in the cytoplasm near the initiation codon, and various indications can be treated by such a mechanism of action. Thus, MPO can be applied to therapeutic agents in almost all fields, such as anticancer drugs, neurological drugs, antivirals, resistant bacteria antibacterial agents, pain therapeutic agents, and immune-related therapeutic agents.

Meanwhile, typical examples of indications through exon skipping include Duchenne muscular dystrophy (DMD), which is a genetic disease, and as a therapeutic agent thereof, eteplirsen from Sarepta is currently marketed under the trade name Exondye 51™.

The corresponding product continues to expand its therapeutic area to hereditary rare incurable disease indications in addition to DMD disease. Thus, MPO derivatives are an area with great potential to be developed as new drugs for various indications, but in order to become more progressive new drugs, it is necessary to solve the problems in various aspects.

Among them, the most important problem to be solved is to have good cell penetration. Therefore, studies for enhancing the degree of cell penetration by developing various methods and derivatives for the polymer MPO have been published. Derivatives that enhance cell penetration known until now are as follows.

The first is a derivative that introduces cell penetrating peptides (CPPs) at the terminal ends of oligonucleotides. Various CPP introductions, such as Penetrain, Tat48-60, transportan, MPG, Oligoarginine, (R-Ahx-R) 4, and Pip2b, have been known until now. However, such CPP introduction has a problem that it is difficult to selectively covalently bind to a specific position of MPO, and production, separation and purification are very difficult, although the economic aspects of requiring expensive production costs are excluded. The second is a derivative that introduces a substituent capable of imparting a positive charge to the backbone and the linker.

For example, representative modified MPO derivatives that enhance cell penetration include the following vivo-morpholinos and PMO plus.

[MPO Derivatives that Enhance Cell Penetration]

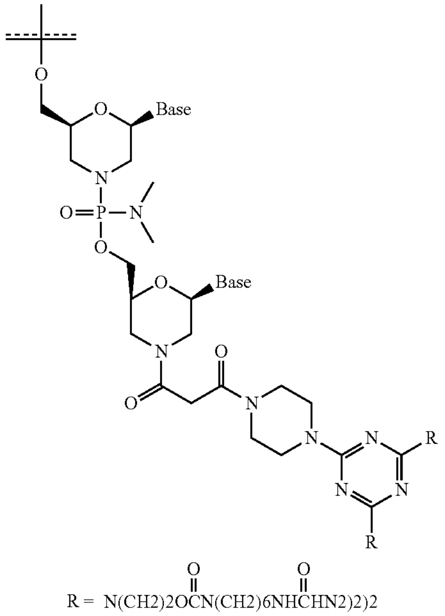

Vivo morpholino

-continued

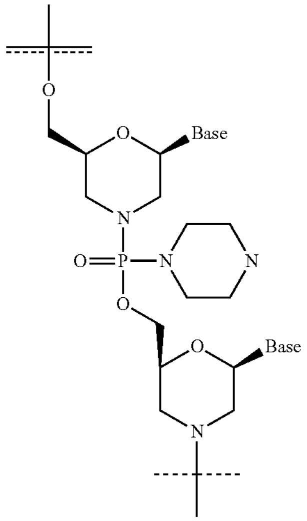

PMO plus

The vivo-morpholinos is an MPO derivative in which triazinyl piperazine substituted with dendrimer octaguanidine at the N-terminus of MPO is a key component, and PMO plus is a derivative that is substituted with piperazine instead of dimethylamide in the phosphorodiamidate linker and provides the cationic properties of the terminal amine, thereby capable of enhancing cell penetration As mentioned above, in terms of developing structural derivatives of MPO to improve cell penetration, researchers so far have made various attempts, such as modifying phosphorodiamidate, which is a linker between monomers, giving cationic properties to the terminal ends, and introducing peptides, as described above.

Meanwhile, several studies (e.g., *Eur. J. org. Chem,* 2013, 1271~1286) that have developed new MPO derivatives by modifying nucleotides are known, among which cytosine derivatives have been mainly studied. However, attempts to introduce pyrrolocytosine derivatives and enhance cell penetration have not yet been well known.

There are substances related to modified cytosine bases that have been applied to various oligonucleotides as shown below.

[Modified Cytosine Base Derivatives]

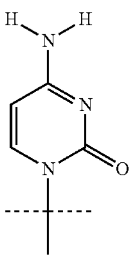

Cytosine

-continued (1)

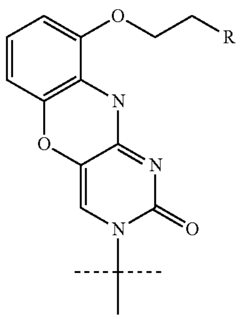

R = NH2, guanidine, (2)

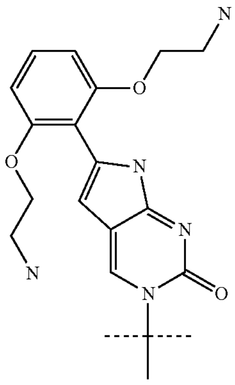

(3)

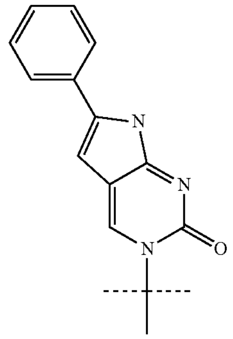

(4)

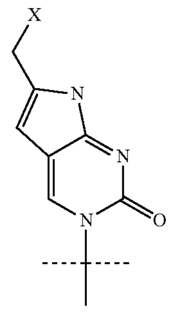

X = OH, NH2

-continued (5)

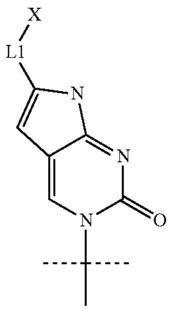

X = NH2
NR1R2

Wherein, (1) is a DNA-phenoxazine derivative, which is known to be a derivative capable of forming a complementary G and G-clamp to a target RNA (*Bioorganic & medicinal chemistry* 25 (2017) 3597~3605).

(2) is a PNA-pyrrolocytosine (pC) derivative (*Bioorganic & medicinal chemistry Letter* 19 (2009) 6181-6184), (3) and (4) are PNA-pyrrolocytosine (pC) derivatives substituted with phenyl or alcohol and amine groups (Nucleoside, nucleotides, and nucleic acids 24 (2005) 581-584). Among them, (5) was disclosed in Korean Patent No. 10-1598423, and is a pyrrolocytosine (pC) derivative in which PNA-aminoalkyl is substituted at the terminal, which is a derivative in which the spatial region of the amino group substituted at the terminal end is extended by giving a methylene radical linker such as L1.

They can mostly utilize G-clamp-mediated bonding to impart great selectivity to complementary guanine bases and stability through concomitant hydrogen bonding. In addition, since the amino group at the terminal end has cationic properties, it is considered to have been designed in anticipation of enhancing the cell surface binding and penetration effect.

Cytosine derivatives modified in this way are mainly applied to PNA. However, there has been no case of applying a cytosine derivative as in the above (5) to MPO yet.

Meanwhile, Korean Patent Registration No. 10-1598423 discloses the preparation of a PNA derivative containing modified cytosine through a synthesis process as shown in the following Reaction Scheme 1.

[Reaction Scheme 1] PNA derivatives containing modified cytosine

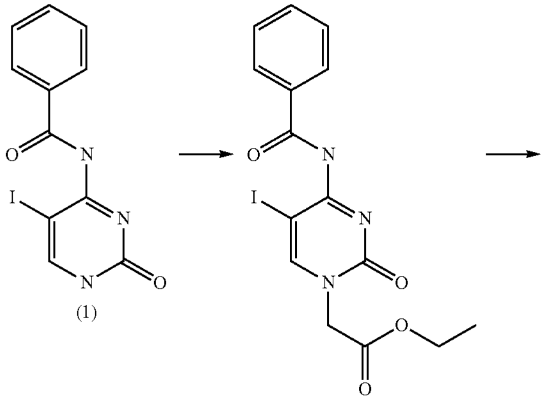

(1) (2)

-continued

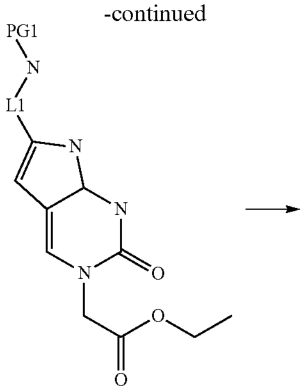

(3)

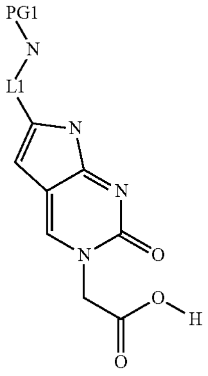

(4)

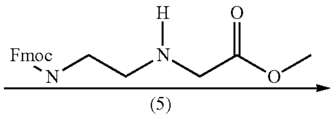

(5)

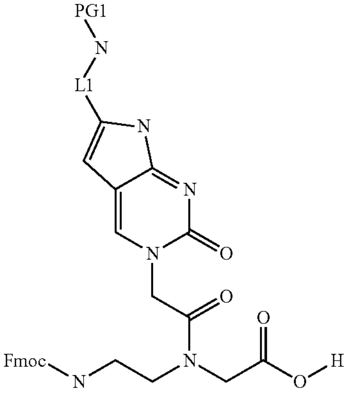

(6)

(wherein, PG1 is a protecting group of an amine group.)

As shown in Reaction Scheme 1, a PNA monomer in which aminoalkyl is substituted at the pyrrole moiety of pyrrolocytosine through a series of synthetic processes is known. The above patent simultaneously discloses not only the modified cytosine but also the modified versions of adenine and guanine in which aminoalkyl is substituted at the terminal end. In addition, modified nucleotides has a limitation in their function is exhibited by binding to PNA.

Given these circumstances, the present inventors have made a long effort to develop morpholino oligonucleotide derivatives that exhibit excellent cell penetration, and as a result, developed a morpholino oligonucleotide (hereinafter, also referred to as "unMPO") that is artificially prepared through based-sequencing of a morpholino oligonucleotide monomer (hereinafter, also referred to as "unMPM") and morpholino oligonucleotide monomers containing cytosine derivatives, especially pyrrolocytosine (Pc), partly with cytosine, or pyrrolocytosine among unnatural nucleotide base instead of all cytosine. Such unMPO is characterized in that it exhibits very excellent cell penetration compared to conventional morpholino oligonucleotide (MPO) derivatives having the same nucleotide sequence composed of only natural nucleotides known by Sarepta and the like.

Due to such excellent cell penetration, unMPO according to the present invention may bring about great development in the field of gene therapeutic agents in the future.

In order to introduce a modified cytosine into a MPO monomer, a synthetic design and technology with high difficulty in terms of the production method are required. Accordingly, the present inventor has completed the present invention after a long effort.

DETAILED DESCRIPTION OF THE INVENTION

Technical Problem

The present invention has been designed to solve the above-mentioned problems, and an object of the present disclosure is to provide a novel morpholino oligonucleotide derivative or a pharmaceutically acceptable salts thereof.

It is another object of the present disclosure to provide a composition comprising the novel morpholino oligonucleotide derivative or a pharmaceutically acceptable salts thereof.

It is yet another object of the present disclosure to provide a gene therapeutic agent comprising the novel morpholino oligonucleotide derivative or a pharmaceutically acceptable salts thereof.

It is a further object of the present disclosure to provide a method for preparing the novel morpholino oligonucleotide derivative

Technical Solution

In order to achieve the above object, the present invention provides a morpholino oligonucleotide (unMPO) comprising at least one unnatural cytosine derivative, particularly a pyrrolocytosine (pC) derivative. The present invention relates to a novel morpholino oligonucleotide derivative (hereinafter also referred to as unMPO) containing at least one type of nucleotide monomer (hereinafter also referred to as unMPM) having pyrrolocytosine (pC) in the field of unnatural nucleic acid base, especially among unnatural cytosine, wherein the morpholino oligonucleotide consists of a phosphorodiamidate bond between morpholino nucleotide monomers. The novel morpholino oligonucleotide derivative in the present invention is useful for sequence-specifically inhibiting or modulating cellular functions and physiological functions mediated by physiologically active molecules having a nucleic acid or nucleic acid domain such as a ribonucleic acid protein. In addition, the novel morpholino oligonucleotide derivative of the present invention are useful for diagnostic purposes due to their sequence-specific binding ability to nucleic acids

Advantageous Effects

A novel morpholino oligonucleotide derivative according to an embodiment of the present invention shows that it has excellent cell penetration as compared to the existing MPO substituted only with natural nucleotides. Since the morpholino oligonucleotide derivative according to the present invention can greatly enhance the degree of cell penetration, which has been the most important problem to be solved in the MPO region, it is considered to be capable of greatly contributing to the development of new drugs in the morpholino oligonucleotide region.

BRIEF DESCRIPTION OF THE DRAWINGS

FIG. 1 is a fluorescence image photograph confirming the degree of cell penetration of tagged MPO-1-Fam and unMPO-1-Fam prepared in Example 16.

DETAILED DESCRIPTION OF THE EMBODIMENTS

Hereinafter, embodiments of the present disclosure will be described

In a specific embodiment of the present invention, there is provided a morpholino oligonucleotide derivative of the following Chemical Formula I:

[Chemical Formula 1]

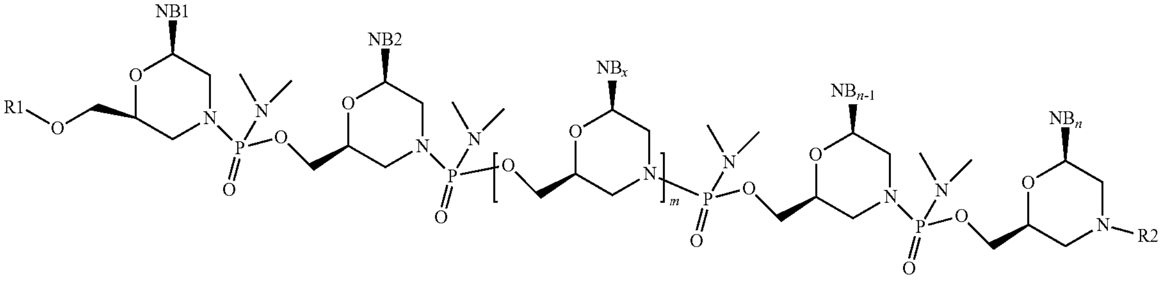

The morpholino oligonucleotide derivative according to the present invention is a morpholino oligonucleotide (unMPO) which is represented by Chemical Formula 1 and comprises at least one unnatural cytosine base, specifically, a pyrrolocytosine (pC)morpholinonucleotide monomer of the following Chemical Formula 2 among the nucleic acid bases (NB):

In Chemical Formula 1, NB means a nucleic acid base.

$NB_1$, $NB_2$, $NB_3$, $NB_{n-1}$ to $NB_n$ are each independently selected from the group consisting of adenine (A) and guanine (G) as a purine group, thymine (T), cytosine (C) and uracil (U) as a pyrimidine group, and pyrrolocytosine (pC) as a modified cytosine as shown in the following:

[Nucleic Acid Bases (NBs)]

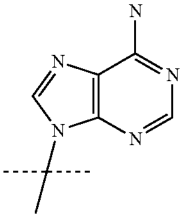

(Adenine, A)

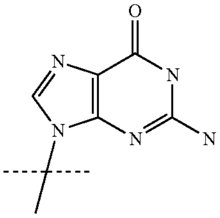

(Guanine, G)

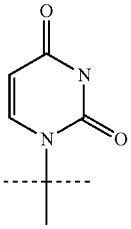

(Uracil, U)

-continued

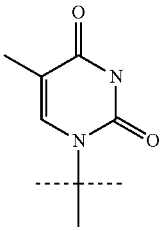

(Thymine, T)

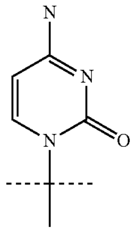

(Cytosine, C)

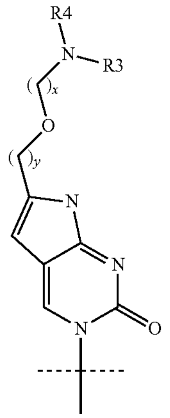

(Pyrrolocytosine, pC)

m is 1 to 40;

n is 1 to 40;

x is 2 to 5;

y is 1 to 3;

R1 and R2 are each independently hydrogen, an alkyl group, an alkyloxyalkyl group containing oxygen, an alkyloxyacyl group, an alkylaminoalkyl group containing nitrogen or an alkylaminoacyl group, each having 1 to 10 carbon atoms.

R3 and R4 are each independently hydrogen or an alkyl group having 1 to 5 carbon atoms, at least one of the $NB_1$, $NB_2$, $NB_3$, $NB_{n-1}$ to $NB_n$ has a pyrrolocytosine (pC) morpholinonucleotide monomer among a modified cytosine.

That is, the present invention provides a morpholino oligonucleotide (unMPO) which is represented by Chemical Formula 1, and has an unnatural cytosine base containing at least one pyrrolocytosine (pC)morpholino nucleotide monomer among unnatural cytosine (NB).

As used herein, an "alkyl" refers to a linear or branched aliphatic saturated hydrocarbon group, and specifically, may be an alkyl having 1 to 10 carbon atoms, an alkyl having 1 to 6 carbon atoms, or an alkyl having 1 to 4 carbon atoms. Examples of such alkyls include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

As used herein, an "acyl" collectively refers to the remaining atomic group RC(═O)-group except OH in the carboxyl group (—COOH), wherein the R is an aromatic or aliphatic hydrocarbon group. Specifically, the R may be an alkyl having 1 to 10 carbon atoms, an alkyl having 1 to 6 carbon atoms, or an alkyl having 1 to 4 carbon atoms.

In a specific embodiment, R1 and R2 may be each independently selected from the group consisting of hydrogen, an alkyl group having 1 to 10 carbon atoms, an alkyl-oxy group having 1 to 10 carbon atoms, an alkyl group having 1 to 10 carbon atoms, an alkyl group having 1 to 10 carbon atoms-oxy-alkyl group having 1 to 10 carbon atoms, and an alkylamino having 1 to 10 carbon atoms-alkyl group having 1 to 10 carbon atoms.

The nucleotide sequence of the nucleic acid base (NB) represented in Chemical Formula 1 is a novel unMPO having a nucleotide sequence capable of complementarily binding to a target gene, specifically, a target RNA or a precursor RNA.

"Complementary," or "complementarity" as used herein refers to the capacity for precise pairing between two nucleotides on one or two oligomeric strands. "Complementary" are terms which are used to indicate a sufficient degree of precise pairing or complementarity over a sufficient number of nucleotides such that stable and specific binding occurs between the oligomeric compound and a target nucleic acid. It will be understood that the sequence of an oligomeric compound is preferably as precisely complementary as possible, but need not be 100% complementary, to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The morpholino oligonucleotides of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted.

The complementarity ratio of the target RNA or precursor RNA region and the antisense compound can be determined routinely using the BLAST program (basic local alignment search tools) and PowerBLAST program known in the art. Percent homology, sequence identity or complementarity, can be determined by, for example, the Gap program (Wisconsin Sequence Analysis Package, Version 8 for Unix, Genetics Computer Group, University Research Park, Madison, Wis.), using default settings, which uses the algorithm of Smith and Waterman (Adv. Appl. Math., (1981) 2,482-489).

The uses of unMPO having pyrrolocytosine, which is a newly modified cytosine, can more selectively bind to the guanine position of the target RNA. In particular, a more important advantage is that it exhibits a very superior degree of cell penetration than MPO with natural cytosine.

Due to these advantages, the morpholino oligonucleotide derivative of the present invention is useful for sequence-specific inhibition or regulation of cellular functions and physiological functions mediated by nucleic acids or physiologically active molecules having a nucleic acid domain such as a ribonucleic acid protein. Also, the morpholino oligonucleotide derivative of the present invention is useful for diagnostic purposes due to their sequence-specific binding ability to nucleic acids. In addition, it is considered that the morpholino oligonucleotide derivative of the present invention can make a great contribution to the development of therapeutic agents for incurable diseases in the morpholino oligonucleotide region.

In order to introduce a modified cytosine into the morpholino nucleotide monomer to prepare the morpholino oligonucleotide according to the present invention, not only the synthesis process significantly different from that of conventionally known PNA, but also a very difficult synthesis technique are required.

Specifically, the morpholino oligonucleotide according to the present invention can be prepared by the following method.

1) synthesizing a morpholino nucleotide monomer having a natural nucleic acid base;
2) synthesizing a morpholino nucleotide monomer substituted with pyrrolocytosine; and
3) synthesizing a morpholino oligonucleotide by a polymer-supported synthesis method using the morpholino nucleotide monomer having a natural nucleic acid base and the morpholino nucleotide monomer substituted with pyrrolocytosine prepared in the steps 1) and 2).

A method for preparing such a morpholino oligonucleotide will be described in each step as follows.

[Synthesis of Morpholino Nucleotide Monomers]

1. Synthesis of Monomers Having Natural Nucleotide Bases

First, in the first step, a morpholino nucleotide monomer substituted with adenine (A-MPM), guanine (G-MPM), thymine (T-MPM), or cytosine (C-MPM) in which the functional group of the nucleic acid base and the amine group of morpholino are protected is synthesized. The protecting group is a known protecting group and can be used without limitation as long as it is a protecting group capable of protecting the functional group of the nucleic acid base and the amine group of morpholino, but non-limiting examples include a trityl group, a benzoyl (Bz) group, isopropylcarbonyl (isobutyryl), an acetyl group, and the like. Several methods for preparing a morpholino nucleotide monomer substituted with adenine (A-MPM), guanine (G-MPM), thymine (T-MPM), and cytosine (C-MPM), in which the functional group of these nucleic acids and the amine group of morpholino are protected, have been disclosed (U.S. Pat. No. 5,185,444, Nucleosides, nucleotides and nucleic acid 31 (2012) 763-782). In the present invention, a monomer having a natural nucleic acid group protected by a protecting group is prepared and used according to the disclosed method. As a specific example, the morpholino nucleotide monomer having a natural nucleic acid base synthesized in the step 1) of the preparation method of the present invention may be any one of the following Chemical Formulas 2) to 5).

[MPM with Natural Nucleotides]

[Chemical Formula 2]

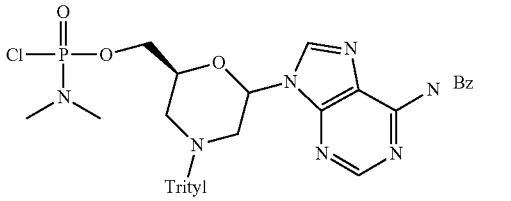

A-MPM

[Chemical Formula 3]

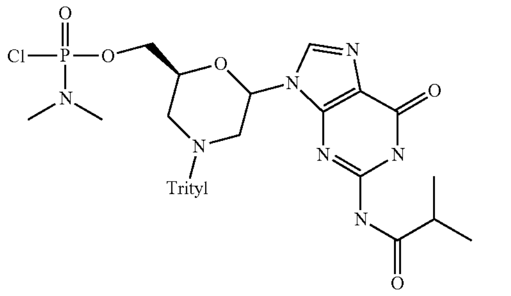

G-MPM

[Chemical Formula 4]

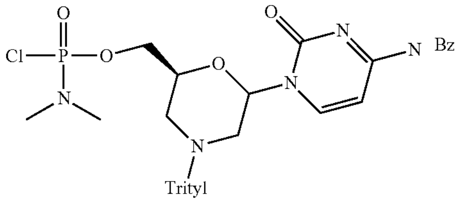

C-MPM

[Chemical Formula 5]

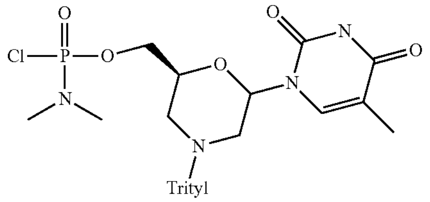

T-MPM

2. Synthesis of Morpholinonucleotide Monomer Substituted with Pyrrolocytosine which is a Modified Nucleic Acid Base The second step is a step of synthesizing a morpholino nucleotide monomer (pC-MPM) derivative having pyrrolocytosine (pC) derivative which is a modified cytosine to prepare unMPO. In order to prepare unMPO by a polymer-supported synthesis method, pC-MPM in which functional groups such as amine groups and alcohol groups are protected with appropriate protecting groups is required.

As a specific example, the morpholino nucleotide monomers having the pyrrolocytosine derivatives are represented by the following Chemical Formulas 6, 6-1, 6-2 and 6-3. Chemical Formula 6 is the general formula of pC-MPM in which functional groups are substituted with pyrrolocytosine (pC) protected by suitable protecting groups, specifically PG3 and PG4, and Chemical Formulas 6-1, 6-2, and 6-3 are specific examples of Chemical Formula 6.

[General Formula of pC-MPM Having Pyrrolocytosine]

[Chemical Formula 6]

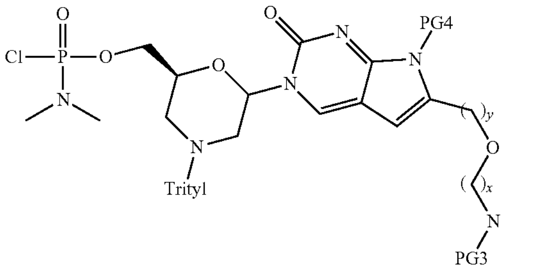

(pC-MPM)

wherein,

PG3 and PG4 must apply sufficiently stable protecting groups so that no side reactions occur during the polymer-supported coupling reaction. Preferably, PG3 is an acid-stable protecting group, and may be selected from the group consisting of fluorenylmethoxycarbonyl (Fmoc), 1,1-dioxobenzo[b]thiophen-2-ylmethoxycarbonyl (Bsmoc), 2-(4-nitrophenylsulfonyl)ethoxycarbonyl (Nsc), 2-(4-sulfophenylsulfonyl)ethoxycarbonyl (Sps), ethanesulfonylethoxycarbonyl (Esc), phthaloyl, tetrachlorophthaloyl (TCP), 2-fluoro fluorenylmethoxycarbonyl (Fmoc (2F)) and 2,7-ditert-butyl fluorenylmethoxycarbonyl (DtBFmoc), and PG4 is a base-stable protecting group and may be selected from the group consisting of tert-butoxycarbonyl (Boc), trityl (Trt), α,α-dimethyl-3,5-dimethylbenzyloxycarbonyl (Ddz), 2-(4-biphenyl) isopropoxycarbonyl (Bpoc) and 2-nitrophenylsulfenyl (Nps), but are not limited thereto.

x is an integer of 1 to 3; and y is an integer of 1 to 3.

[Chemical Formula 6-1]

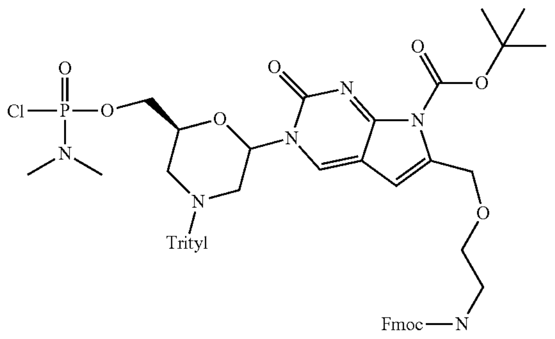

(in pC-MPM, x = 2, y = 1, PG3 = Fmoc, PG4 = Boc)

-continued

[Chemical Formula 6-2]

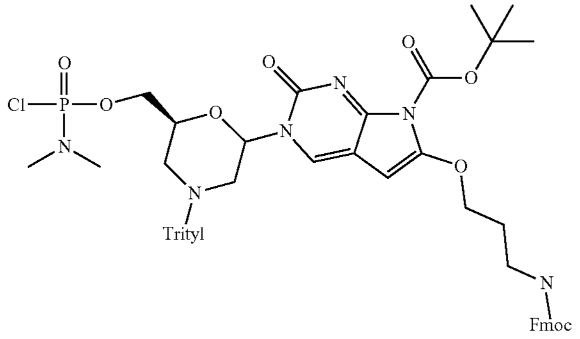

(in pC-MPM, x = 3, y = 1, PG3 = Fmoc, PG4 = Boc)

[Chemical Formula 6-3]

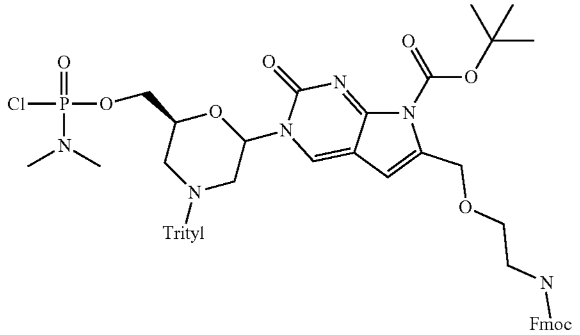

(in pC-MPM, x = 2, y = 2, PG3 = Fmoc, PG4 = Boc)

As a specific example, the step 2) can be performed by a preparation method according to the following Reaction Scheme 2. Reaction Scheme 2 is an example of a method for preparing pC-MPM derivatives in which a functional group such as an amine group and an alcohol group as described above is protected with appropriate protecting groups, and among the morpholino monomers (pC-MPM) substituted with modified cytosine through Reaction Scheme 2, a derivative 5 having x=2 and y=1 can be prepared.

[Reaction Scheme 2] Preparation of modified cytosine-substituted morpholino monomer (pC-MPM) (x = 2, y = 1) derivatives

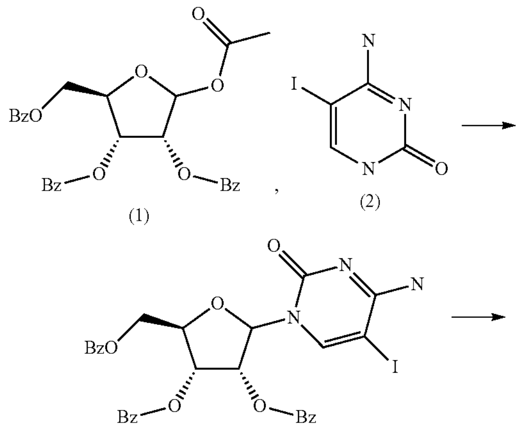

-continued

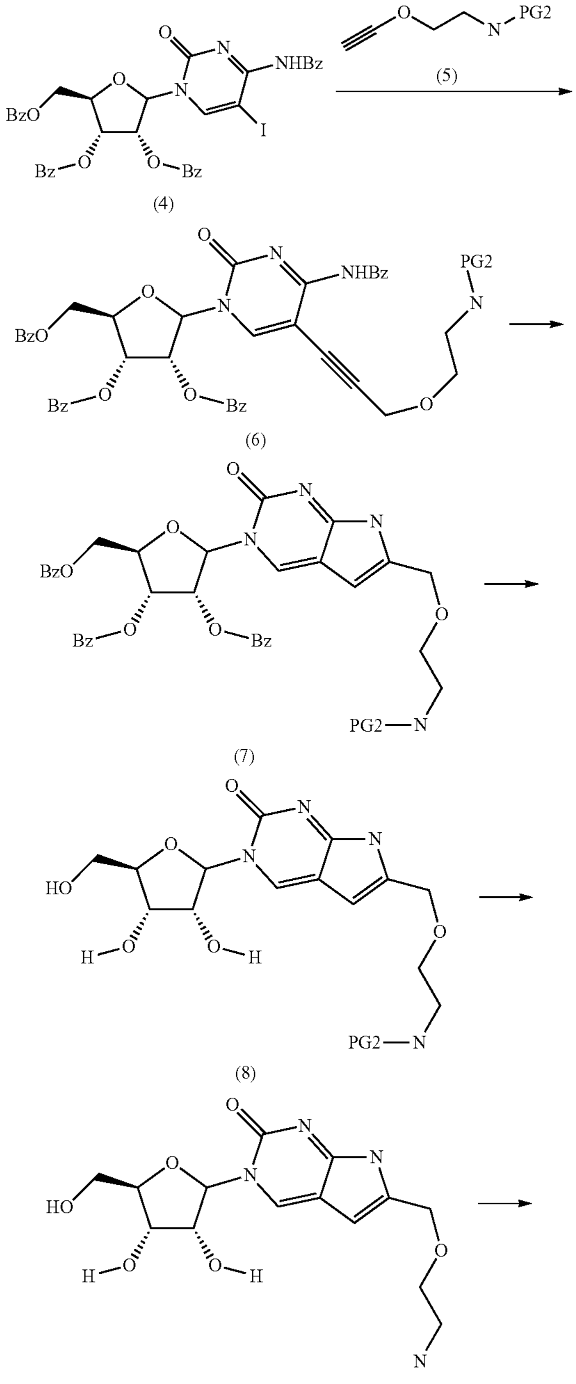

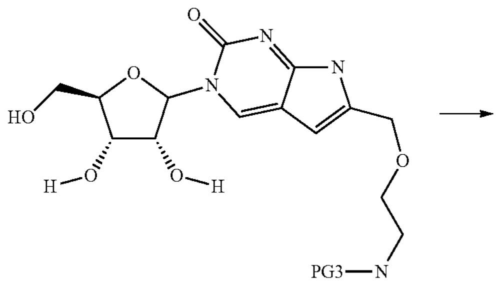

(10)

-continued

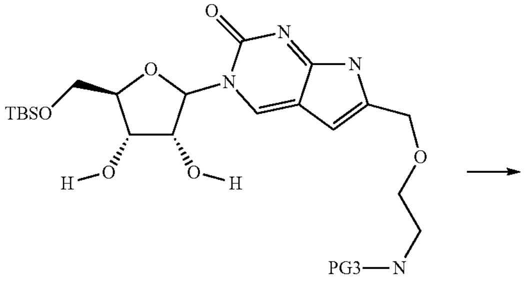

(11)

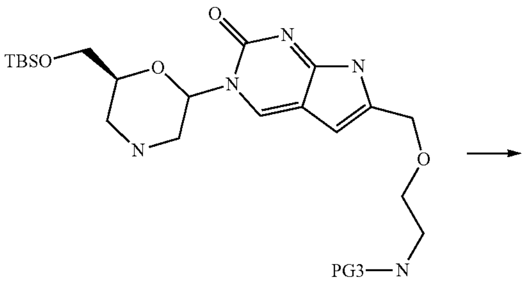

(12)

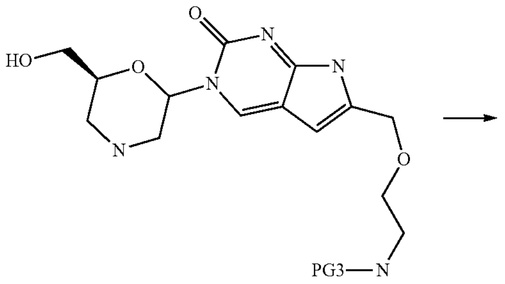

(13)

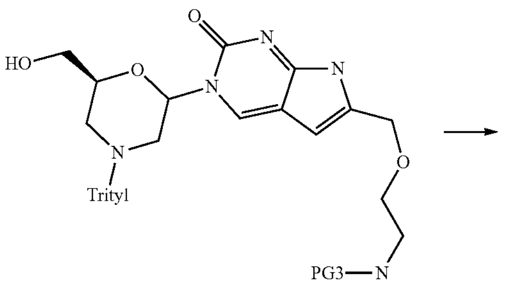

(14)

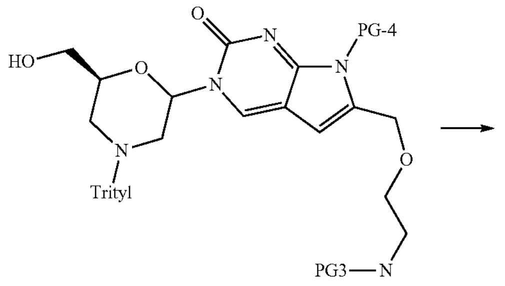

(15)

-continued

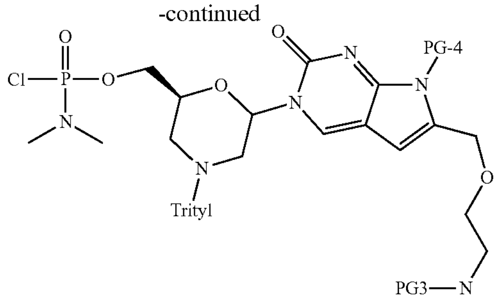

(16, pC-MPM)

A method for preparing a compound of Chemical Formula 6-1, that is, x=2, y=1, which is one of the exemplary compounds of pC-MPM of Chemical Formula 6, is represented by Reaction Scheme 2. The preparation method of Reaction Scheme 2 is described as follows.

First, the first step is a step of preparing Compound (3), and can be performed through glycosylation reaction of 5-iodocytosine (2) using 1-acetyl-2,3,5-tri-O-benzoyl-beta-D-ribofuranose (1) (Preparation Example: heterocyclic letter Vol. 4: (4), 2014, 559-564, effective and regioselective 3-iodination of pyrimidine bases and corresponding nucleosides by inexpensive iodine and sodium nitrite reagent).

The second is a step of protecting the amino group of the prepared Compound (3) with a suitable protecting group, and the protecting group is preferably a benzoyl group (Bz). By protecting the amino group of Compound (3) with such a protecting group, a compound such as Compound (4) is prepared.

Meanwhile, in order to prepare a modified cytosine derivative, a derivative having a triple bond such as 3-{2-(tert-butoxycarbonylamino)ethoxy}-1-propyne (5) is required. Propyne derivatives including Compound (5) and methods for preparing them are disclosed in Korean Patent No. 10-1598423, and these propyne derivatives can be prepared according to the method disclosed in the above issued patent. Here, as PG2, which is a protecting group for protecting the terminal amine of Compound (5), a tert-butoxycarbonyl (Boc) group having stability even in a strong base is preferable.

The third step is a step of reacting the produced Compound (4) and Compound (5) to prepare Compound (6). Specifically, Compound (6) can be prepared through a Sonogashira cross-coupling reaction between Compound (4) and Compound (5).

In the above step, a Pd or Cu catalyst can be used. As the Pd catalyst, tetrakis (triphenylphosphine) palladium (0), bis(triphenylphosphine) palladium(II)dichloride and the like can be used, but bis(triphenylphosphine) palladium(II)dichloride is preferable. Moreover, it is preferable to use a catalytic amount of copper (I) iodine (CuI) as the Cu catalyst. In addition, a tertiary amine is used as an organic base used in the reaction, and examples of such tertiary amine include triethylamine or diisopropylethylamine, and diisopropylethylamine is suitable. As a reaction solvent used in the reaction, aliphatic hydrocarbon solvents such as hexane and pentane; ethers such as diethyl ether, petroleum ether, tetrahydrofuran, and methyltetrahydrofuran; aromatic hydrocarbon solvents such as benzene and toluene; alcohol solvents such as methanol, ethanol, isopropyl alcohol; water; ketone solvents such as acetone and methyl ethyl ketone; ester solvents such as ethyl acetate; nitrile solvents such as acetonitrile; amide solvents such as dimethylformamide and dimethylacetamide; sulfoxide solvents such as dimethylsulfoxide; and a mixed solvent of the above solvents can be used, but a mixed solvent of an amide solvent and an ether solvent is most preferred.

The reaction temperature can range from −30 to 120° C., but the ideal temperature is 0 to 50° C.

The degree of reaction progress during the reaction can be confirmed using HPLC, thin film chromatography (TLC), or the like.

Compound (6) prepared after the reaction may also be separated and purified. As a method for separation and purification, purification methods such as column chromatography or recrystallization can be used.

Hereinafter, unless otherwise specified, the reaction solvent, reaction temperature, confirmation of reaction progress, purification method and the like can be prepared by applying similar conditions.

Fourth, a pyrrolocytosine group is formed from the prepared Compound (6) by an intramolecular cyclization reaction to prepare Compound (7). As the solvent used at this time, a lower alcohol such as ethanol or isopropanol is preferable, and as the reaction temperature, heating reflux conditions are preferable.

Then, the protecting groups protected by alcohol and amine groups are sequentially deprotected to prepare Compound (8) and Compound (9).

Among the reaction conditions that sequentially performs deprotection of Compound (8) and deprotection of Compound (9), the most important point is that reaction conditions that are as mild as possible to the extent that the pyrrolocytosine group introduced into ribofuranose are not separated and removed is required.

Therefore, the benzoyl group of Compound (8) is preferably deprotected using aqueous ammonia in an alcohol solvent. Compound (9) may use trifluoroacetic acid or hydrochloric anhydride, but trifluoroacetic acid is preferred. Thus, Compound (9) can be prepared as a trifluoroacetic acid salt.

Next, the terminal amine of Compound (9) prepared above is protected with a protecting group (PG3) to prepare Compound (10). At this time, as the protecting group of the terminal amine, a protective group stable under acidic conditions is required, and a preferred PG3 protecting group is typically fluorenylmethoxycarbonyl (Fmoc), and similar protecting groups are Fmoc (2F), DtBFmoc, and the like. It can be prepared by using 9-fluorenylmethyl chloroformate (Fmoc-Cl) or 9-fluorenylmethoxycarbonyl N-hydroxysuccinimide (Fmoc-OSu) under a tertiary organic base as the reaction conditions.

Then, the primary alcohol group of Compound (10) prepared above can be protected with a protecting group to prepare Compound (11). At this time, as the protecting group, tert-butyldimethylsilane, tert-butyldiphenylsilane, etc. can be applied, but a tert-butyldimethylsilane (TBS) protecting group is preferable.

In the next step, Compound (12) is prepared using the prepared Compound (11) and sodium periodate ($NaIO_4$). The methods for preparing the morpholino ring of Compound (12) are disclosed in papers and patent literatures such as Nucleosides, nucleotides and nucleic acid 31 (2012) 763 to 782, the entire contents of which are incorporated herein by reference.

It has been generally known that Compound (11) is prepared by subjecting vicinal diol to an oxidative cleavage reaction using sodium periodate ($NaIO_4$), and then subjecting the resulting dialdehyde to a cyclization reaction with intramolecular morpholino via a reduction reaction, and even in the present invention, Compound (12) was able to prepare by synthesizing in an similar manner.

The amine used for subjecting the resulting dialdehyde to a cyclization reaction with intramolecular morpholino is suitably ammonium biborate tetrahydrate ($(NH_4)_2B_4O_7$-$4H_2O$), and as the reducing agent, sodium borohydride, sodium cyanoborohydride ($NaCNBH_3$) and the like can be used, but among these, sodium cyanoborohydride is more preferable.

Then, the protecting group protected by the alcohol group of Compound (12) prepared in the step h) is deprotected under acidic conditions and converted to an alcohol group to obtain Compound (13) in the form of an acid salt. The acid used at this time may be trifluoro acid or anhydrous hydrochloric acid, but it is preferable to use anhydrous hydrochloric acid, which is easy to separate and purify into a crystalline acid salt.

Then, Compound (13) prepared in the step i) is subjected to a substitution reaction using triphenylmethyl chloride (trityl chloride) under weakly basic conditions to prepare Compound (14) in which the secondary amine group of the morpholino ring is protected with a triphenylmethyl (trityl) group.

Suitable solvents used in the reaction are ethers such as tetrahydrofuran and haloalkanes such as dichloromethane, and suitable bases are preferably weak bases of tertiary organic amines such as triethylamine and diisopropylethylamine.

Next, the pyrrolo group of Compound (14) prepared is reacted with a cyclic ether solvent such as anhydrous tetrahydrofuran in the presence of a N,N'-dimethylpyridine catalyst at a temperature of 0 to 50° C. to introduce the protection group, which is protected with a PG4 group to synthesize Compound (15).

Compound (15) is the most important intermediate in the present invention, the pyrrolo group among the morpholino monomers having pyrrolocytosine is weakly basic, and impurities may be generated during the polymer-supported coupling reaction due to the basicity of the pyrrolo group in the polymer supported reaction phase for preparing the oligomer. Therefore, an appropriate protecting group (PG4) is required to minimize the generation of such impurities, and thus PG4 is introduced into the pyrrolo group of Compound (14). The protecting group used for PG4 is preferably a protecting group that can be deprotected by acid, such as acetyl or tert-butoxycarbonyl (Boc), and a tert-butoxycarbonyl (Boc) protecting group is more preferable.

Next, a chloro phosphoramidate functional group is introduced into the primary alcohol group of the morpholino ring in the prepared Compound (15) to synthesize Compound (16). Compound (16) synthesized in this step is finally used in the synthesis of a polymer-supported oligomer as a morpholinonucleotide monomer substituted with pyrrolocytosine, and intermolecular coupling can be performed by introducing chlorophosphoamidate as described above.

The above steps may be performed similarly to the method disclosed in U.S. Pat. No. 8,076,476. Specifically, Compound (15) as a starting material is reacted with N,N-dimethylphosphoamidodichloridate in the presence of a very weak base such as 2,6-lutidine, N-methylimidazole, or N-ethylmorpholine to prepare Compound (16).

The solvent used at this time is preferably a haloalkane such as dichloromethane, a haloalkane such as dichloromethane, an ether such as diethyl ether and tetrahydrofuran, an amide such as dimethylformamide or a mixed solvent thereof, which can dissolve both Compound (15)

and Compound (16) well. A suitable reaction temperature is between-10 and 25° C., since the reactivity is very high.

After the reaction, the step of purifying Compound (16), which is the final morpholinonucleotide monomer prepared, may be further included. Purification can be performed by appropriately selecting a known purification method, but it is preferable to apply a column chromatography using silica gel.

[Synthesis of Morpholino Oligomer: Synthesis of unMPO Using Polymer-Supported Synthesis Method]

The morpholino oligonucleotide according to the present invention is prepared using the natural nucleic acid base and the morpholinonucleotide monomer substituted with pyrrolocytosine as synthesized above.

The natural nucleic acid base and the morpholino nucleotide monomer substituted with pyrrolocytosine are substituted is designed so as to have a nucleotide sequence complementary to a target RNA, so that possibly 5 to 50 mer, but preferably 10 to 40 mer morpholino oligonucleotide can be synthesized by a polymer-supported synthesis method.

Since the nucleotide sequence of the target RNA is very diverse in Gen Bank, and the nucleotide sequence of many genes is disclosed, the unMPO of the present invention having a nucleotide sequence complementary to the target RNA can be synthesized based on such a nucleotide sequence. Due to the characteristics of MPO, a nucleotide sequence can be designed by targeting the nucleotide sequence near the initiation codon of the target RNA.

The unMPO of the present invention can be utilized as an antisense oligonucleotide (ASO) for a very large number of RNAs, but in one example of the present invention, the target material applied in Examples, that is, the target material of the morpholino oligonucleotide is a material having a nucleotide sequence of OH (3')-TCT-CCC-AGC-GTG-CGC-CAT-NH(5') (SEQ ID NO: 1), and the nucleotide sequence of oblimersen ASO known in Annals of Oncology 19 (2008) 1698 to 1705 was selected and performed as a target. Oblimersen is an 18-mer phosphorothiolate oligonucleotide ASO having the same nucleotide sequence, which is an oligonucleotide derivative studied for the purpose of the treatment of cancers such as breast cancer, which has a nucleotide sequence complementary to the first 6 codons of the mRNA expressing Bcl-2.

The nucleotide sequence of unMPO (18-mer) is TunCT-unCunCunC-AGunC-GTG-unCGunC-unCAT. Here, unC (unnatural Cytosine) is a pyrrolocytosine (x=2, y=1)morpholino nucleotide.

Various resins can be applied to a polymer-supported synthesis method, but among them, a preferable resin is an aminomethyl polystyrene (AMPS) resin crosslinked with 1% divinylbenzene (DVB).

Polymer-supported synthesis initially binds an appropriate linker to AMPS, and then, replaces the primary alcohol of the initially used morpholinonucleotide monomer at the terminal end of the linker.

Various linkers capable of binding to AMPS are known, but in the present invention, a succinic anhydride was used as a linker to induce the formation of a carboxylic acid at the terminal end of the morpholinonucleotide oligomer.

The first morpholinonucleotide can be introduced by ester coupling bond with the primary alcohol of the morpholino nucleotide monomer to the carboxylic acid at the terminal end of the polymer resin.

The introduced trityl group of the morpholinonucleotide is then deprotected, and among the morpholinonucleotide monomers represented by Chemical Formulas 2 to 5 and 6, 6-1, 6-2 and 6-3, morpholinonucleotide monomers corresponding to each order are sequentially used to prepare an oligomer via phosphorodiamidate linkage.

Various organic acids such as trifluoroacetic acid can be applied for the deprotection method of the trityl group, but nucleic acid base can be degraded and thus, conditions that are as mild as possible are required. For this reason, it is preferable to apply cyanoacetic acid as the organic acid. In addition, the coupling method for forming a phosphorodiamidate bond with another morpholine nucleotide monomer is performed using a weak base such as diisopropylethylamine. The solvent used at this time is preferably ethers such as tetrahydrofuran, nitriles such as acetonitrile, amides such as dimethylformamide and N-methyl-2-pyrrolidone, haloalkanes such as dichloromethane, their mixed solvents, and the like, which can be well swollen.

Polymer supported synthesis reaction can be performed at a temperature of 0~50° C., but the preferred temperature is 20~30° C. The reaction time is between 10 and 60 minutes, except for special cases.

In addition, in order to check the degree of cell penetration with a microscope such as a confocal microscope, various fluorescent substances can be introduced to the secondary amine terminus of polymer-supported unMPO with the target nucleotide sequence. Fluorescein, cyanine, TAMRA and the like can be applied as fluorescent materials, but it is preferable to apply Fam (fluorescein). The carboxylic acid of Fam and the amine of a linker can be subjected to an amidization reaction to introduce a Fam derivative to which the linker is bound. As the linker, amino acids are widely used, and the use of 6-aminohexanoic acid is particularly preferable. Further, there are various derivatives of Fam, but a fluorescent material activated with carboxylic acid was used as 6-[fluorescein-5(6)-carboxyamido] hexanoic acid N-hydroxysuccinimide which 6-carboxyfluorescein (6-Fam) and 6-aminohexanoic acid commonly used are bound. By forming an amide bond at the N-terminus of a morpholino oligonucleotide supported on a polymer using the fluorescent substance and protected with a functional group, a morpholino oligonucleotide to which a fluorescent material is bound can be prepared. However, the present invention is not limited thereto.

After completing the polymer-supported synthesis, a step is required to remove the protecting group of unMPO attaching to a polymer chain. The conditions for deprotecting the protecting group attaching to the nucleic acid base are preferably a method of simultaneously removing the benzoyl group, isobutyryl group, Fmoc group, and the like protected from the ester linker of AMPS and the nucleic acid base.

As the deprotection method, deprotection can be performed using a base selected from the group consisting of methylamine, aqueous ammonia, and a mixed base. The reaction time is 0.5 to 24 hours, preferably 1 to 5 hours.

Furthermore, the separated unMPO can be concentrated under reduced pressure at a low temperature and then solidified to prepare unMPO before purification.

Then, in order to prepare a pure unMPO, reverse-phase column purification can be performed using prep-HPLC to prepare the target material.

In another aspect, the present invention provides a composition comprising the novel morpholino oligonucleotide derivative or a pharmaceutically acceptable salt thereof.

The morpholino oligonucleotide derivative of the present invention or a pharmaceutically acceptable salt thereof can easily pass through mammalian cell membranes and sequence-specifically bind to intracellular nucleic acids or nucleic acid proteins to affect or change cell functions. The morpholino oligonucleotide derivative of Chemical Formula I or a pharmaceutically acceptable salt thereof can bind strongly to mRNA and strongly inhibit protein synthesis by ribosome. The morpholino oligonucleotide derivative of the present invention or a pharmaceutically acceptable salt thereof can bind strongly to pre-mRNA and alter the splicing of pre-mRNA to mRNA. Further, the morpholino oligonucleotide derivative of the present invention or a pharmaceutically acceptable salt thereof can bind strongly to microRNA and inhibit mRNA degradation induced by microRNA. The morpholino oligonucleotide derivative of Chemical Formula I or a pharmaceutically acceptable salt thereof can predictably bind to the nucleic acid domain of a ribonucleic acid protein, such as telomerase, and modulate physiological functions. The morpholino oligonucleotide derivative of the present invention or a pharmaceutically acceptable salt thereof can bind to a gene and regulate transcription of the gene. The morpholino oligonucleotide derivative of Chemical Formula I or a pharmaceutically acceptable salt thereof can bind to a viral gene or a transcript thereof and inhibit viral proliferation. The morpholino oligonucleotide derivative of the present invention or a pharmaceutically acceptable salt thereof can sequence-specifically bind to a nucleic acid or nucleic acid protein in mammalian cells and affect cellular functions different from those described above. Further, the morpholino oligonucleotide derivative of the present invention or a pharmaceutically acceptable salt thereof can bind strongly to bacterial mRNA, nucleic acid, or gene, thereby inhibiting bacterial growth or changing the bacterial biosynthesis profile. When the morpholino oligonucleotide derivative of the present invention or a pharmaceutically acceptable salt thereof binds to its complementary DNA counterpart, it is highly sensitive to base mismatch and is suitable for detecting single nucleotide polymorphisms (SNPs) with high accuracy. Since the morpholino oligonucleotide derivative of the present invention or a pharmaceutically acceptable salt thereof can bind strongly to a complementary DNA with high sequence specificity, it can be useful for gene profiling. If a morpholino oligonucleotide derivative of Chemical Formula I or a pharmaceutically acceptable salt thereof is appropriately tagged with a chromophore, e.g., a fluorophore, it is useful for locating or retrieving molecules having nucleic acid sites, such as telomeres, within cells. The morpholino oligonucleotide derivative of the present invention or a pharmaceutically acceptable salt thereof may be useful for various diagnostic or analytical purposes other than those described above.

In another aspect, the present invention provides a gene therapeutic agent comprising the morpholino oligonucleotide and a pharmaceutically acceptable diluent or carrier.

Diseases that can be treated with the gene therapeutic agent are diseases that can be treated by regulating the activity or inactivity of the target gene, and is not limited. However, for example, as the application of therapeutic agents utilizing antisensing to inhibit protein production of target mRNA, it can be applied to inflammatory therapeutic agents, such as autoimmune diseases, anticancer drugs, antiviral drugs, antibiotics, etc. As antisensing applied to exon skipping, therapeutic agents for Duchenne Muscular Dystrophy genetic disease can be typically mentioned. Other hereditary neuromuscular diseases include a wide variety of diseases, such as spinal muscular atrophy (SMA), myotonic atrophy type 1 (DM1) Urich's disease.

The gene therapeutic agent according to the present invention comprises a morpholino oligonucleotide derivative comprising at least one morpholinonucleotide containing pyrrolocytosine as an active ingredient, and thus, exhibits an excellent effect in the treatment of diseases related to target genes due to its excellent cell penetration.

The gene therapeutic agent of the present invention may be administered orally or parenterally in accordance with a desired method. For parenteral administration, it is preferable to select skin external or intrathecal, intraperitoneal, rectal, intravenous, intramuscular, subcutaneous, intrathoracic or intracerebrovascular injection modes.

The dose of the gene therapeutic agent according to the present invention varies depending on the patient's body weight, age, sex, health condition, diet, administration time, administration method, excretion rate, and severity of disease, and is not intended to limit the scope of the present invention in any way. Individual doses specifically contain the amount of the active drug administered at one time.

The gene therapeutic agents of the present invention can be used alone or in combination with methods using surgery, radiotherapy, hormone therapy, chemotherapy and biological response modifiers.

DETAILED DESCRIPTION OF THE EMBODIMENTS

Hereinafter, the present invention will be described in more detail by way of examples. However, these examples are provided for illustrative purposes only and for a better understanding of the present invention, and are not intended to limit the scope of the present invention.

The specifications for the instruments used for the analysis of embodiments of the present invention are as follows.

A bruker 400 MHz was used for NMR, TripleTOF5600+ was used for high-performance mass spectrometry (LC-Q/TOF-MS), and Agilent 1100 series was used for HPLC. And as a device for measuring cell permeability, the confocal laser scanning microscope used a GE Delta Vision Elite High Resolution Microscope.

Example 1: Preparation of Compound (4) of Reaction Scheme 2:5-iodo-N4,2',3'5'-tetrabenzoylcytidine 80 g of 5-iodo-2',3',5'-tri-O-benzoylcytidine, which is Compound (3) disclosed in Heterocyclic letter Vol. 4: (4), 2014, 559-564, was added to 240 ml of dichloromethane, to which 39.8 g of benzoyl anhydride was added, and then the mixture was reacted at 40° C. for 3 days.

After completion of the reaction, the mixture was extracted three times with 300 ml of purified water, washed, and dried over anhydrous sodium sulfate. After filtering the drying agent, the solvent was concentrated under reduced pressure to obtain an oily residue. 600 ml of absolute ethanol was added to the residue, and the mixture was stirred for 1 day, filtered and dried to obtain 84.7 g of Compound (4). (Yield 91.8%)

(Compound (4) NMR DMSO-d6) 12.73 (1H, s), 8.48 (1H, s) 7.41~8.18 (20H, m) 6.24~6.25 (1H, d, J=3.6 Hz) 5.96~6.02z (2H, m) 4.67~4.81 (3H, m)

Maldi-TOF: [M+23]=808.15

Example 2: Preparation of Compound (7) of Reaction Scheme 2 (PG2 is Boc): (2R,3R,4R,5S)-2-[(benzoyloxy)methyl]-5-[6-(2-((tert-butoxycarbonyl)amino)ethoxy)methyl]-2-oxo-2H-pyrrolo[2,3-d]pyrimidin-3(7H)-yl)tetrahydrofuran-3,4-diyl Dibenzoate 30 g of Compound (5) of Reaction Scheme 2 was dissolved in 90 ml of dimethylformamide and 30 ml of tetrahydrofuran under a nitrogen atmosphere, to which 11.4 g of 3-[2-(tert-butoxycarbonylamino)ethoxy]-1-propyne was added and the temperature was maintained at 25° C.

13.3 ml of Diisopropylethylamine was added, and 1.34 g of Pd(Ph3P)2Cl2 and 1.45 g of CuI were sequentially added. When the starting material disappeared after reacting at room temperature for 24 hours, 300 ml of ethyl acetate and 300 ml of purified water were added and extracted. The extract was washed twice with 300 ml of purified water, and washed with 200 ml of saturated brine. The organic layer was dried over anhydrous sodium sulfate, filtered and concentrated under reduced pressure to obtain Compound (6) as a brown oil. The following reaction was carried out without purifying the concentrated residue to prepare Compound (7).

300 ml of absolute ethanol was added to Compound (6), the mixture was heated and refluxed for 24 hours, so that an intramolecular cyclization reaction proceeded. The progress of the reaction was confirmed by thin film chromatography (MC:MeOH=10:1 rf~0.5). After completion of the reaction, the solvent was concentrated under reduced pressure, to which 300 ml of ethyl acetate and 200 ml of purified water were added and extracted. The extract was washed with 100 ml of saturated brine, dried over anhydrous sodium sulfate, filtered, and then concentrated under reduced pressure to obtain Compound (7) as a brown oil.

500 ml of Isopropyl ether was added to the oily residue, solidified, filtered and dried to obtain 25 g of Compound (7). (Total yield=87%)

(Compound (7) NMR DMSO-d6) 11.3 (1H, s), 8.76 (1H, s), 7.35~8.15 (15H, m), 6.87 (1H, d), 6.20 (1H, s) 5.90~5.95 (1H, m) 5.54 (1H, s), 5.27 (1H, s), 5.09 (1H, s), 4.06~4.39 (2H, s), 3.77~3.97 (4H, m), 3.78 (1H, m) 3.61 (1H, m), 3.40~3.42 (2H, t), 3.15~3.17 (2H, m), 1.36 (9H, s), Maldi-TOF: [M+23]=775.53

Example 3: Preparation of Compound (8) of Reaction Scheme 2 (PG2 is Boc): tert-Butyl(2-((3-((2S,3R,4S,5R)-3,4-dihydroxy-5-(hydroxymethyl)tetrahydrofuran-2-yl)-2-oxo-3,7-dihydro-2H-pyrrolo[2,3-d]pyrimidin-6-yl)methoxy)ethyl)carbamate 30 g of Compound (7) of Reaction Scheme 2 was dissolved in 80 ml of methanol and 30 ml of tetrahydrofuran under a nitrogen atmosphere, to which 80 g of 35% aqueous ammonia was added and reacted at 25° C. for 2 days.

It was confirmed by thin film chromatography (MC:MeOH=5:1 rf~0.5) that the three benzoyl groups were removed. After completion of the reaction, the pressure was reduced once the starting material disappeared.

The concentrated residue was purified by silica gel column chromatography (separated while adjusting at a column developing solvent: MC:MeOH=8:1 to 5:1) to obtain 15 g of a brown amorphous solid compound (8). (Yield=85%)

(Compound (8) NMR DMSO-d6) 11.34 (1H, s), 8.76 (1H, s), 6.87 (1H, d), 6.2 (1H, s) 5.90~5.95 (1H, m) 5.54 (1H, s), 5.27 (1H, s), 5.09 (1H, s), 4.06~4.39 (2H, s), 3.77~3.97 (4H, m), 3.78 (1H, m) 3.61 (1H, m), 3.40~3.42 (2H, t), 3.15~3.17 (2H, m), 1.36 (9H, s), Maldi-TOF: [M+23]=463.14

Example 4: Preparation of Trifluoroacetic Acid Salt of Compound (9) of Reaction Scheme 2: 6-((2-aminoethoxy)methyl)-3-((2S,3R,4S,5R)-3,4-dihydroxy-5-(hydroxymethyl)tetrahydrofuran-2-yl)-3,7-dihydro-2H-pyrrolo[2,3-d]pyrimidin-2-one Tetrafluoro Acid Salt 11.6 g of Anisole and 116 g of dichloromethane were added to 11.6 g of Compound (8), and suspended. The suspended solution was maintained at 10° C., and 30 ml of trifluoroacetic acid was slowly added dropwise while maintaining 25° C. After confirming the progress of the reaction and the completion of the reaction through thin-film chromatography (acetonitrile:water=4:1, rf=0.3), it was concentrated under reduced pressure at an external temperature of 40° C. or less. 50 g of Ethyl acetate and 100 g of diethyl ether were added to the concentrated residue, and the resulting solid was filtered, and vacuum-dried at 30° C. to obtain 10.5 g of the trifluoroacetic acid salt form of Compound (9) (Yield=87.7%).

(Compound (9) NMR DMSO-d6) 11.41 (1H, s), 8.85 (1H, s), 6.28 (1H, s), 4.50 (2H, s) 3.97~3.99 (2H, m), 3.40~3.42 (2H, m), 3.19~3.32 (2H, m), 3.11~3.17 (2H, m), 3.03~3.07 (2H, m), Maldi-TOF: [M+23]=363.13

Example 5: Preparation of Compound (10) of Reaction Scheme 2 (PG 3 is Fmoc): (9H-fluoren-9-yl)methyl(2-((3-((2S,3R,4S,5R)-3,4-dihydroxy-5-(hydroxymethyl)tetrahydrofuran-2-work)-2-oxo-3,7-dihydro-2H-pyrrolo[2,3-d]pyrimidin-6-yl)methoxy)ethyl)carbamate 10 g of Compound (9) of Reaction Scheme 2 was dissolved in 100 ml of ethanol under a nitrogen atmosphere, and 5.56 g of triethylamine was added thereto. The reaction temperature was maintained below 10° C., and 6.3 g of 9-fluorenylmethyl chloroformate (Fmoc-Cl) was added dropwise little by little.

After confirming the completion of the reaction through thin film chromatography (MC:MeOH=5:1 rf~0.5), the reaction solution was concentrated under reduced pressure at 35° C. or less, and the concentrated residue was purified by column chromatography using silica gel (eluent: MC:MeOH=5:1) to obtain 9.5 g of light brown amorphous solid compound (10). (Yield=76.7%)

(Compound 10 NMR DMSO-d6) 11.30 (1H, s), 8.78 (1H, s), 7.67~7.90 (2H, m), 7.41~7.43 (2H, m), 7.30~7.43 (4H, m), 6.18 (1H, s), 5.99 (1H, s), 4.49 (2H, s), 4.41 (1H, s), 3.94~3.99 (2H, m) 3.47~3.51 (2H, m) 3.34~3.45 (2H, m), 3.17~3.19 (2H, m)

Maldi-TOF: [M+23]=585.36.

Example 6: Preparation of Compound (11) of Reaction Scheme 2 (PG 3 is Fmoc): (9H-fluoren-9-yl)methyl(2-((3-((2S,3R,4S,5R)-3,4-dihydroxy-5-(((tert-butyldimethylsilyl)oxy)methyl)-3,4-dihydroxy-tetrahydrofuran-2-yl)-2-oxo-3,7-dihydro-2H-pyrrolo[2,3-d]pyrimidin-6-yl)methoxy)ethyl) carbamate 9.1 g of Compound (10) of Reaction Scheme 2 was added to and dissolved in 45 ml of pyridine, to which 0.2 g of N,N'-dimethylaminopyridine was added and the temperature was maintained at 15° C.

6 g of Tert-butal dimethyl chlorosilane was added by dividing into ⅓ at 12 hour intervals and the mixture was reacted. After completion of the reaction, the reaction solvent was concentrated under reduced pressure, dissolved in 100 ml of ethyl acetate, and washed with 100 ml of saturated brine. The organic layer was dried over anhydrous sodium sulfate, filtered, and the concentrated under reduced pressure. After concentration, 100 ml of isopropyl ether was added to the residue, and the resulting solid was filtered to obtain 8.2 g of the target compound (11). (Yield=74.9%)

(Compound (11) NMR DMSO-d6) 11.32 (1H, s), 8.79 (1H, s), 7.67~7.90 (2H, m), 7.40~7.45 (2H, m), 7.30~7.45 (4H, m), 6.18 (1H, s), 5.99 (1H, s), 4.50 (2H, s), 4.40 (1H, s), 3.91~4.00 (2H, m) 3.45~3.53 (2H, m), 3.32~3.45 (2H, m), 3.15~3. (2H, m), 2.45~2.50 (6H, m), 0.90 (9H, s)

Maldi-TOF: [M+23]=699.51

Example 7: Preparation of Compound (12) of Reaction Scheme 2 (PG3 is Fmoc): (9H-fluoren-9-yl)methyl(2-((3-((2S,6S)-6-(((tert-butyldimethylsilyl)oxy)methyl)morpholin-2-yl)-2-oxo-3,7-dihydro-2H-pyrrolo[2,3-d]pyrimidin-6-yl)methoxy)ethyl) carbamate 8.0 g of Compound (11) of Reaction Scheme 2 was added to and dissolved in 150 ml of methanol, and 7.2 g of ammonium biborate tetrahydrate ((NH4)2B4O7-4H2O) was added to the reaction solution. 7.2 g of Sodium periodate (NaIO4) was added thereto, and the mixture was reacted while stirring at 20±5° C. for 5 hours. After confirming that Compound 11 has disappeared, the reaction mixture was filtered through celite, and 1.5 g of sodium cyanoborohydride (NaCNBH3) was added to the filtrate. Immediately thereafter, 1.4 g of acetic acid was added thereto. The mixture was reacted at 20±5° C. for 2 hours, and concentrated under reduced pressure. 150 ml of ethyl acetate was added to the residue, and 100 ml of purified water was added thereto. After extraction, the organic layer was washed with 50 ml of saturated brine and the organic layer was dried over anhydrous sodium sulfate. After filtration, 100 ml of isopropyl ether was added dropwise to the residue concentrated under reduced pressure, and the resulting solid was filtered, and vacuum-dried at 30° C. to obtain 5.4 g of Compound (12). (Yield=69.2%)

(Compound 12 NMR DMSO-d6) 11.31 (1H, s), 8.75 (1H, s), 7.67~7.90 (2H, m), 7.41~7.43 (2H, m), 7.30~7.43 (4H, m), 6.20 (1H, s), 5.48~5.55 (1H, m), 4.05~4.44 (2H, s), 3.63~3.67 (1H, m), 3.50~3.61 (2H, m), 3.34~3.45 (2H, m), 3.09~3.19 (2H, m), 2.74~2.79 (2H, m), 2.60~2.67 (1H, m), 2.30~2.38 (1H, m), 2.47~2.49 (6H, m), 0.89 (9H, s)

Maldi-TOF: [M+23]=682.45

Example 8: Preparation of Compound (13) of Reaction Scheme 2 (PG3 is Fmoc): (9H-fluoren-9-yl)methyl(2-((3-((2S,6S)-6-(hydroxymethyl)morpholin-2-yl)-2-oxo-3,7-dihydro-2H-pyrrolo[2,3-d]pyrimidin-6-yl)methoxy)ethyl)carbamate 9.6 g of Compound (12) of Reaction Scheme 2 was added to and dissolved in 200 ml of absolute ethanol, to which 20 ml of hydrochloric acid solution dissolved in 13% isopropyl alcohol was added at 20±5° C., and the mixture was reacted while stirring for 3 hours. The reaction solution was concentrated under reduced pressure. 200 ml of Acetone was added to the residue, and the resulting solid was filtered. After filtration, the filtrate was washed with 30 ml of acetone to obtain 7.2 g of Compound (13) in hydrochloride form. (Yield=85%)

70 ml of Purified water and 20 ml of tetrahydrofuran were added to and dissolved in the crude compound (13) hydrochloride, to which 40 ml of 5% sodium bicarbonate was added. The mixture was reacted for 2 hours, and 100 ml of tetrahydrofuran and 50 ml of ethyl acetate were sequentially added to the reaction solution. The separated water layer was removed, 50 ml of saturated brine was added to the organic layer and washed. The organic layer was separated, dried over anhydrous sodium sulfate, filtered and concentrated. The concentrated residue was solidified with a mixed solvent of acetone and ethyl acetate, filtered, and washed with ethyl acetate. The result was vacuum-dried at 30° C. to obtain 5.5 g of Compound (13) having a free amine. (Yield=82%).

(Compound (13) NMR DMSO-d6) 11.35 (1H, s), 8.75 (1H, s), 7.67~7.90 (2H, m), 7.41~7.43 (2H, m), 7.30~7.43 (4H, m), 6.20 (1H, s), 5.48~5.55 (1H, m), 4.05~4.44 (2H, s), 3.63~3.67 (1H, m), 3.50~3.61 (2H, t), 3.34~3.45 (2H, m), 3.09~3.19 (2H, m), 2.74~2.79 (2H, m), 2.60~2.67 (1H, m), 2.30~2.38 (1H, m), Maldi-TOF: [M+23]=568.45

Example 9: Preparation of Compound (14) of Reaction Scheme 2 (PG3 is Fmoc): (9H-fluoren-9-yl)methyl(2-((3-((2S,6S)-6-(hydroxymethyl)-4-tritylmorpholin-2-yl)-2-oxo-3,7-dihydro-2H-pyrrolo[2,3-d]pyrimidin-6-yl)methoxy)ethyl)carbamate 8.4 g of Compound (13) of Reaction Scheme 2 was added to and dissolved in 150 ml of dichloromethane, to which 3.2 ml of triethylamine was added, and the temperature was maintained at 10±5° C. 5.2 g of Trityl chloride was added by dividing into ¼ portions at 30 minute intervals and the mixture was reacted for 5 hours. After completion of the reaction, 100 ml of purified water was added, the organic layer was extracted and washed with 50 ml of saturated brine. The separated organic layer was dried over anhydrous sodium sulfate, filtered and concentrated. The concentrated residue was solidified with ethyl ether, filtered, and then washed with ethyl ether. The result was vacuum-dried at 30° C. to obtain 9.58 g of Compound (14). (Yield=79%)

(Compound (14) NMR DMSO-d6) 11.35 (1H, s), 8.75 (1H, s), 7.67~7.90 (2H, m), 7.67~7.90 (2H, m), 7.00~7.60 (21H, m), 6.20 (1H, s), 5.48~5.55 (1H, m), 4.05~4.44 (2H, s), 3.63~3.67 (1H, m), 3.50~3.61 (2H, t), 3.34~3.45 (2H, m), 3.09~3.19 (2H, m), 2.74~2.79 (2H, m), 2.60~2.67 (1H, m), 2.30~2.38 (1H, m), Maldi-TOF: [M+23]=810.63

Example 10: Preparation of Compound (15) of Reaction Scheme 2 (PG3 is Fmoc, PG4 is Boc): tert-Butyl-6-((2-((((9H-fluoren-9-yl)methoxy)carbonyl)amino)ethoxy)methyl)-3-((2S,6S)-6-(hydroxymethyl)-4-tritylmorpholin-2-yl)-2-oxo-3,7-dihydro-2H-pyrrolo[2,3-d]pyrimidine-7-(3H)-carboxylate 1.64 g of Compound (14) of Reaction Scheme 2 was added to and dissolved in 20 ml of anhydrous tetrahydrofuran, to which 25 mg of dimethylpyridine was added, and the temperature was maintained at 0±5° C. A solution of 0.5 g of di-tert-butyl dicarbonate (Boc anhydride) dissolved in 5 ml of tetrahydrofuran was slowly added dropwise to the reaction solution for 1 hour. The mixture was reacted while stirring at 20±5° C. for 5 hours. After completion of the reaction, the reaction product was concentrated under reduced pressure, the concentrated residue was purified by silica gel column chromatography (eluent: ethyl acetate:n-hexane=3:1) and solidified with ethyl ether. The result was vacuum-dried at 30° C. to obtain 1.55 g of Compound (15). (Yield=83.9%)

(Compound 15 NMR $CDCl_3$) 8.02 (1H, s), 7.87 (1H, s), 7.74~7.62 (2H, m), 7.41~7.43 (2H, d), 7.17~7.60 (23H, m), 6.57~6.59 (1H, m), 6.37~6.40 (1H, m), 5.19 (1H, m), 4.67 (2H, m), 4.36~4.44 (3H, m), 4.19~4.23 (2H, m), 3.59~3.68 (6H, m), 3.41~3.43 (2H, m), 3.13~3.23 (2H, m), 1.58~1.65 (9H, d)

Maldi-TOF: [M+23]=911.02

Example 11: Preparation of Compound (16-1) of Reaction Scheme 2 (PG3 is Fmoc, PG4 is Boc): tert-Butyl-6-((2-((((9H-fluoren-9-yl)methoxy)carbonyl)amino)ethoxy)methyl)-3-((2S,6S)-6-(((chloro (dimethylamino)phosphoryl)oxy)methyl)-4-tritylmorpholin-2-yl)-2-oxo-3,7-dihydro-2H-pyrrolo[2,3-d]pyrimidine-7-(3H)-carboxylate 2.0 g of N,N'-dimethylphosphonamidic dichloride was dissolved in 30 ml of anhydrous tetrahydrofuran, and the temperature was maintained at 0±5° C. 1.22 g of N-methylimidazole was added thereto. 5.5 g of Compound (15) of Reaction Scheme 2 was added to the reaction solution, and the mixture was reacted for 10 minutes. 0.78 ml of N-ethyl morpholine was added to the reaction solution, and the mixture was reacted while stirring for 3 hours.

After completion of the reaction, the reaction solution was added to a mixed solution of 50 ml of 1M $KH_2PO_4$ aqueous solution and 50 ml of ethyl acetate. The organic layer was separated, washed with saturated brine, and dried over anhydrous sodium sulfate.

The drying agent was filtered and concentrated under reduced pressure. The resulting residue was separated and purified by silica gel column chromatography using a developing solution (ethyl acetate:n-hexane=2:1). The result was solidified with ethyl ether and vacuum-dried at 30° C. to obtain 5.1 g of Compound (16-1). (Yield=81.2%)

(Compound (16-1) NMR $CDCl_3$) 8.02 (1H, s), 7.87 (1H, s), 7.74~7.62 (2H, m), 7.41~7.43 (2H, d), 7.17~7.60 (23H, m), 6.57~6.59 (1H, m), 6.37~6.40 (1H, m), 5.19 (1H, m), 4.67 (2H, m), 4.36~4.44 (3H, m), 4.19~4.23 (2H, m), 3.59~3.68 (6H, m), 3.41~3.43 (2H, m), 3.13~3.23 (2H, m), 2.65 (6H, dd), 1.58~1.65 (9H, d)

Maldi-TOF: [M+23]=1036.13

Example 12: Preparation of Compound (16-2) (x=3, y=1, PG3=Fmoc, PG4=Boc) in pC-MPM of Chemical Formula 6: tert-Butyl-6-((2-((((9H-fluoren-9-yl)methoxy)carbonyl)amino)propoxy)methyl)-3-((2S,6S)-6-(((chloro(dimethylamino)phosphoryl) oxy)methyl)-4-tritylmorpholin-2-yl)-2-oxo-3,7-dihydro-2H-pyrrolo[2,3-d]pyrimidine-7-(3H)-carboxylate The target compound (16-2) was prepared in the same manner as in the preparation method of Examples 2 to 11 by using 3-[2-(tert-butoxycarbonylamino) propyloxy]-1-propyne, and using the same proportion of equivalents with respect to the intermediates and reagents used, (Compound (16-2) NMR $CDCl_3$) 8.02 (1H, s), 7.87 (1H, s), 7.74~7.62 (2H, m), 7.41~7.43 (2H, d), 7.17~7.60 (23H, m), 6.57~6.59 (1H, m), 6.37~6.40 (1H, m), 5.19 (1H, m), 4.67 (2H, m), 4.36~4.44 (3H, m), 4.19~4.23 (2H, m), 3.59~3.68 (6H, m), 3.41~3.43 (2H, m), 3.13~3.23 (2H, m), 2.65 (6H, dd), 1.60~1.70 (2H, m) 1.58~1.65 (9H, d)

Maldi-TOF: [M+23]=1050.03

Example 13: Preparation of Compound (16-3) (x=2, y=2, PG3=Fmoc, PG4=Boc) in pC-MPM of Chemical Formula 6: tert-Butyl-6-((2-((((9H-fluoren-9-yl)methoxy)carbonyl)amino)ethoxy)ethyl)-3-((2S,6S)-6-(((chloro(dimethylamino)phosphoryl) oxy)methyl)-4-tritylmorpholin-2-yl)-2-oxo-3,7-dihydro-2H-pyrrolo[2,3-d]pyrimidine-7-(3H)-carboxylate The target compound (16-3) was prepared in the same manner as in the preparation method of Examples 2 to 11 using 4-[2-(tert-butoxycarbonylamino)ethoxy]-1-butyne, and using the same proportion of equivalents with respect to the intermediates and reagents used, (Compound (16-3) NMR $CDCl_3$)) 8.02 (1H, s), 7.87 (1H, s), 7.74~7.62 (2H, m), 7.41~7.43 (2H, d), 7.17~7.60 (23H, m), 6.57~6.59 (1H, m), 6.37~6.40 (1H, m), 5.19 (1H, m), 4.67 (2H, m), 4.36~4.44 (3H, m), 4.19~4.23 (2H, m), 3.59~3.68 (6H, m), 3.41~3.43 (2H, m), 3.13~3.23 (2H, m), 2.65 (6H, dd), 1.60~1.70 (2H, m) 1.58~1.65 (9H, d)

Maldi-TOF: [M+23]=1050.25

Example 14: Synthesis of MPO Having the Nucleotide Sequence of TCT-CCC-AGC-GTG-CGC-CAT by Polymer-Supported Synthesis Method 1. Introduction of a Succinylamide Linker into Aminomethyl Polystyrene Resin (AMPS)

6 ml of N-methylpyrrolidone (NMP) was added to 0.8 g of aminomethylpolystyrene resin (1% DVD crosslinked, 0.8~1.0 mmole/g, 100~200 mesh), swollen while shaking at a speed of 100 rpm for 20 minutes, and filtered.

A reaction solution in which 0.8 mg of succinyl anhydride and 40 mg of DMAP were dissolved in 2 ml of NMP and 2 ml of pyridine was added, and then the mixture was reacted while shaking at a speed of 100 rpm for 2 hours, and filtered. 4 ml of NMP was washed with shaking for 5 minutes and filtered. This process was repeated 3 times. Then, the process was performed 3 times in which a reaction solution in which 1.0 ml of diethyl pyrocarbonate was dissolved in 5 ml of dichloromethane was added, and the mixture was reacted while shaking at 100 rpm for 15 minutes, filtered, and washed with 5 ml of dichloromethane while shaking for 3 minutes. The process was repeated 3 times in which a reaction solution in which 0.5 g of cyanoacetic acid was dissolved in 5 ml of dichloromethane was added, and the mixture was reacted while shaking at a speed of 100 rpm for 15 minutes, filtered, and with 5 ml of dichloromethane while shaking for 3 minutes. The polymer support to which the resulting succinylamide group was linked was dried under nitrogen to obtain 1.06 g.

2) Introduction of T-MPM (AMPS-Linker-T) to the Polymer Support to which the Succinylamide Group is Linked The process was repeated 3 times in which 220 mg of N-trityl morpholinothymidine, 60 mg of DMAP and 100 mg of diisopropylcarbodiimide (DIC) were added to 0.5 g of the polymer support to which the succinylamide group was linked, 5 ml of a mixed solvent in a ratio of tetrahydrofuran: dichloromethane:NMP=2:1:1 was added, and the mixture was reacted while shaking at a speed of 100 rpm for 12 hours, filtered, and washed with 5 ml of the same proportion of solvent while shaking for 3 minutes.

After washing, the process was repeated 3 times in which 3 ml of 11% cyanoacetic acid solution (acetonitrile:dichloromethane=3:1 mixed solution) was added, and then the mixture was reacted while shaking at a speed of 100 rpm for 10 minutes, filtered and washed with 5 ml of dichloromethane while shaking for 3 minutes.

Then, the process was repeated 3 times in which 2 ml of 5% diisopropylethylamine solution (isopropyl alcohol:dichloromethane=1:3) was reacted while shaking at a speed of 100 rpm for 10 minutes, filtered, and washed with 5 ml of dichloromethane while shaking for 3 minutes.

3) Introduction of MPO (TCT-CCC-AGC-GTG-CGC-CAT) Based on the Nucleotide Sequence A-MPM, C-MPM, T-MPM and G-MPM were added to the AMPS-Linker-T prepared above, and were sequentially prepared based on the nucleotide sequence as follows.

The amount of MPM used at this time was 320 mg/(dichloromethane:THF=1:2) mixed solvent 3 ml in the case of A-MPM, 320 mg/(dichloromethane:THF=1:2) mixed solvent 3 ml in the case of G-MPM, 230 mg/(dichloromethane:THF=1:2) mixed solvent 3 ml in the case of T-MPM, 340 mg/(dichloromethane:THF=1:2) mixed solvent 3 ml in the case of C-MPM, and 280 mg in the case of T-MPM, respectively.

The coupling reaction using each MPM was as follows.

First, the process was repeated 3 times in which 160 mg of N-ethylmorpholine and 5 ml of a mixed solution of tetrahydrofuran:dichloromethane=2:1 were added to AMPS-Linker-T, and then 340 mg of C-MPM was added, and the mixture was reacted while shaking at a speed of 100 rpm for 3 hours, filtered, and washed with 5 ml of the same proportion of solvent while shaking for 3 minutes.

After washing, the process was repeated 3 times in which 3 ml of 11% (w/w) cyanoacetic acid solution (acetonitrile:dichloromethane=3:1 mixed solution) was added and then the mixture was reacted while shaking at a speed of 100 rpm for 10 minutes, filtered, and washed with 5 ml of dichloromethane while shaking for 3 minutes.

Then, the process was repeated 3 times in which 2 ml of 5% diisopropylethylamine solution (isopropyl alcohol:dichloromethane=1:3) was reacted while shaking at a speed of 100 rpm for 10 minutes twice, filtered, and washed with 5 ml of dichloromethane while shaking for 3 minutes.

Subsequently, the reaction was performed as described above using the MPM corresponding to the following. Thereby, 980 mg of AMPS-Linker-TCT-CCC-AGC-GTG-CGC-CAT was prepared.

4) Separation from Polymer-Supported Resin 900 mg of the AMPS-Linker-TCT-CCC-AGC-GTG-CGC-CAT was added to a flask, to which 5 ml of ethanol, 5 ml of aqueous ammonia, and 10 ml of 7% methylamine/tetrahydrofuran were added, and subjected to deprotection reaction while stirring at 300 rpm for 24 hours. After completion of the reaction, the resin was filtered off, and the mother liquor was concentrated under reduced pressure, and dried to obtain 85 mg (MPO-1) of MPO having the TCT-CCC-AGC-GTG-CGC-CAT sequence.

Example 15: Synthesis of unMPO Having the Nucleotide Sequence of TunCT-CunCunC-AGunC-GTG-unCGunC-unCAT by Polymer-Supported Synthesis Method 80 mg (MPO-2) of unMPO having the nucleotide sequence of TunCT-CunCC-AGunC-GTG-unCGunC-unCAT was obtained in the same manner as in Example 14 by using 460 mg of the corresponding pC-MPM.

Example 16: Tags of MPO-1 and unMPO-1 Compounds Using Fam

The cell permeability was visually measured using a confocal laser scanning microscope. To tag with fluorescein (Fam) fluorescent material, MPO-1 and unMPO-1 tagged with Fam were prepared by the following method.

The process was repeated 3 times in which 100 mg of AMPS-Linker-TCT-CCC-AGC-GTG-CGC-CAT and 120 mg of AMPS-Linker-TunCT-CunCC-AGunC-GTG-unCGC-unCAT prepared in Examples 15 to 16 were reacted with 50 mg of 6-[fluorescein-5(6)-carboxyamido]hexanoic acid N-hydroxysuccinimide in 5 ml of a mixed solvent of tetrahydrofuran:NMP=1:1 while shaking at a speed of 100 rpm for 3 hours, filtered, and washed with 5 ml of the same proportion of solvent while shaking for 3 minutes.

Then, the obtained AMPS-Linker-TCT-CCC-AGC-GTG-CGC-CAT-Hx-Fam and AMPS-Linker-TunCT-CunCC-AGunC-GTG-unCGC-unCAT-Hx-Fam were separated and purified from the polymer-supported resin in the same manner to obtain tagged TCT-CCC-AGC-GTG-CGC-CAT-Hx-Fam (MPO-1-Fam) and TunCT-CunCC-AGunC-GTG-unCGC-unCAT-Hx-Fam (unMPO-1-Fam).

Example 17: Confirmation of the Degree of Cell Penetration of Tagged MPO-1 and unMPO-1 Compounds In order to confirm the degree of cell penetration of the tagged MPO-1-Fam and unMPO-1-Fam prepared in Example 16, HeLa cells were seeded at 20,000 to 50,000 cells/well, depending on the growth rate of the cell line in an 8-well chamber (Lab-Tek chamber slide system). Each cell was cultured at 37° C. under 5% carbon dioxide atmosphere for 16~24 hours. The medium was replaced with 250 μL fresh DMEM medium (containing no FBS) containing MPO-1 and unMPO-1 at a concentration of 5 μM, respectively, and then cultured for 1 hour, 2 hours, 12 hours and 24 hours, respectively. Each cell was then washed twice with FBS, and then replaced with DMEM medium (containing FBS).

Fluorescence images of respective cells were confirmed with a GE/DeltaVision Elite High Resolution Microscope (100× objective). FIG. 1 shows a photograph of the degree of cell penetration for MPO-1-Fam and unMPO-1-Fam, and confirms that MPO-1-Fam has almost no cell penetration, whereas unMPO-1-Fam shows very high cell penetration in proportion to time.

The invention claimed is:

1. A morpholino nucleotide monomer substituted with pyrrolocytosine of the following Chemical Formula 6:

[Chemical Formula 6]

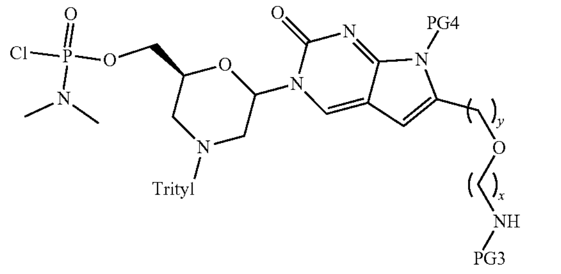

(pC-MPM)

wherein:

PG3 is selected from the group consisting of fluorenylmethoxycarbonyl (Fmoc), 1,1-dioxobenzo[b]thiophen-2-ylmethoxycarbonyl (Bsmoc), 2-(4-nitrophenylsulfonyl)ethoxycarbonyl (Nsc), 2-(4-sulfophenylsulfonyl)ethoxycarbonyl (Sps), ethanesulfonylethoxycarbonyl (Esc), phthaloyl, tetrachlorophthaloyl (TCP), 2-fluoro fluorenylmethoxycarbonyl (Fmoc (2F)) and 2,7-ditert-butyl fluorenylmethoxycarbonyl (DtBFmoc);

PG4 is selected from the group consisting of tert-butoxycarbonyl (Boc), trityl (Trt), α,α-dimethyl-3,5-dimethylbenzyloxycarbonyl (Ddz), 2-(4-biphenyl) isopropoxycarbonyl (Bpoc) and 2-nitrophenylsulfenyl (Nps);

x is an integer of 1 to 3; and y is an integer of 1 to 3.

2. The morpholino nucleotide monomer according to claim 1 wherein:

the morpholinonucleotide monomer substituted with pyrrolocytosine of Chemical Formula 6 is represented by a structure selected from the group consisting of the following Chemical Formulas 6-1, 6-2 and 6-3:

[Chemical Formula 6-1]

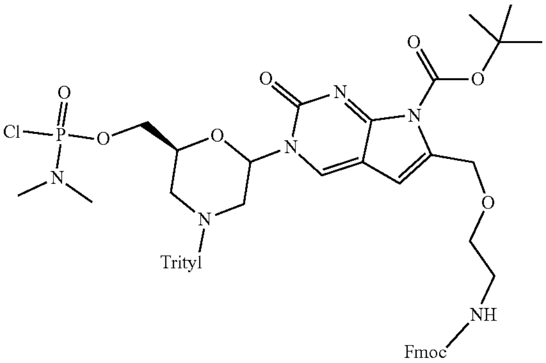

-continued

[Chemical Formula 6-2]

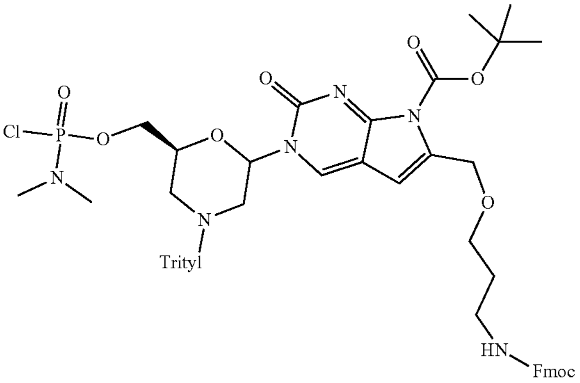

[Chemical Formula 6-3]

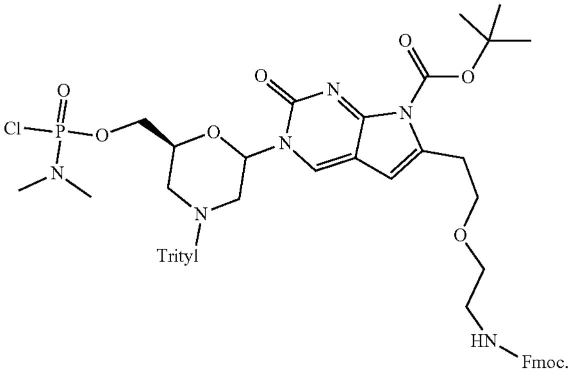

* * * * *